US011517574B2

(12) United States Patent
Czaplewski et al.

(10) Patent No.: US 11,517,574 B2
(45) Date of Patent: *Dec. 6, 2022

(54) LINEZOLID FORMULATIONS

(71) Applicant: PERSICA PHARMACEUTICALS LTD., Canterbury (GB)

(72) Inventors: Lloyd Czaplewski, Canterbury (GB); Sarah Guest, Canterbury (GB)

(73) Assignee: Persica Pharmaceuticals Ltd., Canterbury (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/764,468

(22) PCT Filed: Nov. 16, 2018

(86) PCT No.: PCT/GB2018/053319
§ 371 (c)(1),
(2) Date: May 15, 2020

(87) PCT Pub. No.: WO2019/097242
PCT Pub. Date: May 23, 2019

(65) Prior Publication Data
US 2020/0352952 A1 Nov. 12, 2020

Related U.S. Application Data

(60) Provisional application No. 62/587,101, filed on Nov. 16, 2017.

(51) Int. Cl.
*A61K 31/5355* (2006.01)
*A61P 19/02* (2006.01)
*A61P 31/04* (2006.01)
*A61K 9/00* (2006.01)
*A61K 9/06* (2006.01)
*A61K 47/18* (2017.01)
*A61K 47/34* (2017.01)

(52) U.S. Cl.
CPC ........ *A61K 31/5355* (2013.01); *A61K 9/0019* (2013.01); *A61K 9/06* (2013.01); *A61K 47/18* (2013.01); *A61K 47/34* (2013.01); *A61P 19/02* (2018.01); *A61P 31/04* (2018.01)

(58) Field of Classification Search
None
See application file for complete search history.

(56) References Cited

U.S. PATENT DOCUMENTS

| 5,702,717 | A | 12/1997 | Cha et al. | |
|---|---|---|---|---|
| 2001/0051621 | A1* | 12/2001 | Bergren | C07D 263/22 514/236.2 |
| 2001/0056206 | A1 | 12/2001 | Lorenzi et al. | |
| 2005/0143678 | A1* | 6/2005 | Schwarz | A61B 17/12099 601/4 |
| 2010/0036000 | A1 | 2/2010 | Lighter et al. | |
| 2011/0076231 | A1 | 3/2011 | Schwarz et al. | |
| 2012/0263797 | A1* | 10/2012 | D'Agostino | A61L 27/52 424/602 |
| 2012/0277199 | A1 | 11/2012 | Ye et al. | |
| 2013/0164224 | A1 | 6/2013 | Kim et al. | |
| 2013/0177603 | A1* | 7/2013 | Gutierro Aduriz | A61P 25/18 424/400 |
| 2013/0195988 | A1 | 8/2013 | Duan et al. | |
| 2014/0275977 | A1 | 9/2014 | Curley et al. | |
| 2014/0302051 | A1 | 10/2014 | Askari et al. | |
| 2016/0310699 | A1 | 10/2016 | Al-Jilaihawi | |
| 2017/0290948 | A1 | 10/2017 | Schwarz et al. | |

FOREIGN PATENT DOCUMENTS

| CN | 104586768 A | 5/2011 |
|---|---|---|
| RU | 2495662 C2 | 10/2013 |
| WO | 2001057035 A1 | 8/2001 |
| WO | 02/30395 A1 | 4/2002 |
| WO | 2004084703 A2 | 10/2004 |
| WO | 2011049958 A2 | 4/2011 |
| WO | 2011056528 A2 | 5/2011 |
| WO | 2011140519 A2 | 11/2011 |
| WO | 2015/059623 A1 | 4/2015 |
| WO | 2015059623 A1 | 4/2015 |
| WO | 2017/019440 A1 | 2/2017 |
| WO | 2018/091895 A1 | 5/2018 |
| WO | 2019/060869 A1 | 3/2019 |

OTHER PUBLICATIONS

Zheng et al. Fluid Phase Equilibria V 432 pp. 18-27. (Year: 2016).*
Biochemical, Reagent Kits Offer Scientists Good Return on Investment [online], Ahern (1995). Retrieved from the internet: <http://www.the-scientist.library.upenn.edu/yr1995/july/tools_950724.html>. (Year: 1995).*
Nguygen and Lee, "Injectable biodegradable hydrogels" (2010) Macromol. Biosci. 10:563-579.
Gong et al., "Thermosensitive polymeric hydrogels as drug delivery systems" (2013) Current Medicinal Chemistry 20:79-94.
Nie et al., "Thermoreversible Pluronic® F127-based hydrogel containing liposomes for the controlled delivery of paclitaxel: in vitro drug release, cell cytotoxicity,and uptake studies" (2011) International Journal of Nanomedicine 6:151-156.
Pandit et al. "Gelation of Pluronic F127-polyethylene glycol mixtures: relationship to PEG molecular weight" (1998) Drug Dev. Ind. Pharm 24(2):183-186.
Dudli et al., "Inflammatory response of disc cells against Propionibacterium acnes depends on the presence of lumbar Modic changes" (2018) eur Spine J. 27(5):1013-1020.
Zamora et al., "Effect of Propionibacterium acnes (PA) injection on intervertebral disc degeneration in a rat model: Does it mimic modic changes?" (2017) Orthop Traumatol Surg Res. 103(5):795-799.

(Continued)

*Primary Examiner* — Katherine Peebles
(74) *Attorney, Agent, or Firm* — Wolf, Greenfield & Sacks, P.C.

(57) ABSTRACT

The present invention relates to injectable, thermosensitive hydrogel compositions comprising linezolid for relieving and/or treating chronic low back pain (CLBP).

14 Claims, 7 Drawing Sheets

(56) References Cited

OTHER PUBLICATIONS

Knezevic, N.N. et al., "Treatment of chronic low back pain—new approaches on the horizon" (2017) J. of Pain Research 10:1111-1123.
Slaby, O. et al., "Is IL-1β further evidence for the role of Propionibacterium acnes in degenerative disc disease? Lessons from the study of the inflammatory skin condition acne vulgaris" (2018) Frontiers in Cellular and Infection Microbiology vol. 8 | Article 272 | 7 pages.
Communication pursuant to Article 94(3) EPC dated Apr. 14, 2021 in counterpart European application No. 18808077.4 entitled, Linezolid Formulations.
International Search Report and Written Opinion dated Feb. 14, 2019 in corresponding application PCT/GB2018/053319, entitled Linezolid Formulations.
Chenite, A. et al., "Novel injectable neutral solutions of chitosan form biodegradable gels in situ" (2000) Biomaterials 21:2155-2161.
Lee, S. et la., "Regional delivery of vancomycin using pluronic F-127 to inhibit methicillin resistant *Staphylococcus aureus* (MRSA) growth in chronic otitis media in vitro and in vivo" (2004) Journal of Controlled Release 96:1-7.
Radivojša, M. at al., Thermoreversible in situ gelling poloxamer-based systems with chitosan nanocomplexes for prolonged subcutaneous delivery of heparin: Design and in vitro evaluation (2013) European Journal of Pharmaceutical Sciences 50(1):93-101.
Urquhart, D.M. et al., "Could low grade bacterial infection contribute to low back pain? A systematic review" (2015) BMC Medicine 13:13.
Veyries, M.L. et al., "Controlled release of vancomycin from Poloxamer 407 gels" (1999) International Journal of Pharmaceutics 192:183-193.
Veyries, M.L. et al., Control of Staphylococcal Adhesion to Polymethylmethacrylate and Enhancement of Susceptibility to Antibiotics by Poloxamer 407 (2000) Antimicrobial Agents and Chemotherapy 44(4):1093-1096.
Karolewicz, B. et al., "In vitro evaluation of the gels properties prepared thermosensitive polymers as vehicles for administration substance by injection" (2011) Polim Med. 41(4):3-15.
Fayad, F. et al., "Relation of inflammatory modic changes to intradiscal steroid injection outcome in chronic low back pain" (2007) Eur Spine J 16:925-931.
Lee et al., Intradiscal drug delivery system for the treatment of low back pain, J Biomed Mater Res A. Jan. 2010;92(1):378-85. doi: 10.1002/jbm.a.32377.
Fleege., C. et al., "Systemic and local antibiotic therapy for conservatively and surgically treated spondylodiscitis" (2012) The orthopedist 41:727-735.
International Search Report dated Feb. 7, 2018 in corresponding PCT application No. PCT/GB2017/053447 entitled Antibiotic Formulations for Lower Back Pain.
Search Report dated Nov. 12, 2021 in corresponding Singapore application No. 11202003537T entitled Linezolid Formulations.
Written Opinion dated Nov. 12, 2021 in corresponding Singapore application No. 11202003537T entitled Linezolid Formulations.
Office Action dated Nov. 12, 2021 in corresponding Russian application No. 2020115866 entitled Linezolid Formulations.
Search Report dated Nov. 12, 2021 in corresponding Russian application No. 2020115866 entitled Linezolid Formulations.
Klessig et al., The use of intradiscal antibiotics for discography: an in vitro study of gentamicin, cefazolin, and clindamycin. Spine (Phila PA 1976). Aug. 1, 2003;28(15): 1735-8. doi: 10.1097/01. BRS.0000087301.71177.85.

* cited by examiner

Linezolid Form II pre-micronisation  Linezolid Form II post-micronisation

LINEZOLID FORMULATIONS

CROSS REFERENCE TO RELATED APPLICATIONS

This application is a 35 U.S.C. § 371 U.S. National Stage Entry of International Application No. PCT/GB2018/053319 filed Nov. 16, 2018, entitled, LINEZOLID FORMULATIONS, which claims the benefit of priority to U.S. Provisional Patent Application No. 62/587,101, filed Nov. 16, 2017, entitled, LINEZOLID FORMULATIONS, the contents of which are herein incorporated by reference in their entirety.

FIELD OF THE INVENTION

The present invention provides linezolid formulations, methods and manufactures useful for chronic low back pain treatment. In one aspect of the invention, the linezolid formulation comprises linezolid form II suspension, iohexol and poloxamer 407, and is injectable.

BACKGROUND OF THE INVENTION

Chronic Low back pain (CLBP) is common among the general population worldwide. A positive association between Modic changes (bone edema) on MRI and non-specific LBP with a mean odds ratio (OR) of 4.5 has been observed. Jensen et al. reviewed that the prevalence for any type of Modic changes (e.g., Types I-III) in patients with non-specific CLBP was 46% as opposed to 6% in the general population (Jensen et al., *Eur. Spine J.* 2008, 17:1407-1422).

Modic changes, characterized by edema (or inflammation) in vertebrae, are likely caused by low-grade infection of the disc tissue, where disc/endplate damage and the persistence of an inflammatory stimulus create predisposing conditions. *Propionibacterium acnes* (*P. acnes*) inside non-pyogenic intervertebral discs has been shown to be one pathogen causing Modic changes (e.g., Type I) and nonspecific low back pain (Stirling et al. *Lancet*, 2001, 357:2024-2025; Agarwal et al. *Spine J.* 2010, 10: S45-S46; Albert et al., *Eur Spine J.*, 2013, 22(4): 690-696; Capoor et al., *PLoS One*, 2016, 11(8):e0161676. doi: 10.1371; and Capoor et al., *PLos One*, 2017, 12(4): e0174518.doi:10.1371). Disc cells can develop an inflammatory response to *P. acnes* infection (Dudli et al., *Eur Spine J.*, 2017, Sep. 7. doi: 10.1007/s00586-017-5291-4). *P. acnes* isolated from a patient associated with Modic changes and disc degeneration, when inoculated into the intervertebral discs, can induce inflammatory reaction, intervertebral disc degeneration and Modic changes (Chen et al., *Biomed Res Int.* 2016: 9612437. doi: 10.1155/2016/9612437. Epub 2016 Jan. 26; and Chen et al., *Int Orthop.* 2016, 40(6):1291-1298; and Dudli et al., *J Orthop Res.* 2016, 34(8):1447-1455). Studies done in animals also show that *P. acnes* infection in disc can induce degeneration of the disc and Modic changes (Zamora et al., *Orthop Traumatol Surg Res.*, 2017, 103(5): 795-799; Shan et al., *Spine*, 2017, Apr. 10. doi: 10.1097/BRS.0000000000002192; and Shan et al, *J Bone Joint Am.*, 2017, 99(6): 472-481). Strains of *P. acnes* associated with tissue infections also express hyaluronic acid degrading enzymes which may contribute to disc degeneration. (Nazipi et. al., Microorganisms. 2017 Sep. 12; 5(3). pii: E57. doi: 10.3390/microorganisms5030057).

It is hypothesized that anaerobic bacteria (like *P. acnes*) from mouth and skin may gain access to the disc. Local inflammation in the adjacent bone may be a secondary effect due to cytokine and propionic acid production, where the infection is in the disc and the Modic change is a "side effect" manifested in the bone (Albert et al., *Eur Spine J.*, 2013, 22(4): 690-696).

Antibiotic therapy may be effective in the treatment of CLBP associated with Modic changes). Several studies have shown that oral administration of antibiotics such as amoxicillin-clavulanate can have a clinically important and statistically significant (p<0.001) improvement in all outcome measures in patients with chronic LBP (Albert et al., *Br. J. Sports Med.* 2008, 42(12): 969-973; and Albert et al. *Eur Spine J.* 2013, 22(4): 697-707). These results provided support for the hypothesis that bacterial infection may play a role in CLBP with Modic changes.

Although several non-surgical treatment approaches including intradiscal injections of steroid, anti-TNF-α antibody and bisphosphonates have demonstrated some short-term efficacy in non-replicated clinical studies in reducing Modic changes and CLBP, none of these approaches is successful and causes controversial results. On this background, there is a need in the art for modalities to address the treatment, alleviation, prevention, and/or mitigation of pain found to be coincident with diseases, conditions or disorders of the bones, joints, ligaments and/or tendons, especially those associated with Modic changes or bone edema. The present invention provides linezolid formulations to fill this need. Linezolid is an antibiotic used for the treatment of infections caused by Gram-positive bacteria that are resistant to other antibiotics. *P. acnes* clinical isolates which are resistant to linezolid (MIC>4 μg/ml) have not been widely reported. The linezolid formulations provide an effective delivery of linezolid to the diseased disc and vertebrae, therefore improve treatment efficacy of Modic changes and CLBP.

SUMMARY OF THE INVENTION

The present invention provides injectable formulations suitable for delivering linezolid to the infected spinal sites for treating, preventing, ameliorating, and/or mitigating one or more types of pain, or phenotypic presentations coincident with a clinical condition of the bones, joints, ligaments, or tendons. Kits, packages and methods of manufacturing and using the same are also provided.

In accord with the present invention, linezolid formulations are made as suspensions which form hydrogels in situ in responding to the warm body temperature. The formulation of the present invention is thermosensitive and injectable.

In some embodiments, the formulation of the present invention comprises an effective amount of linezolid. In some aspects, linezolid is linezolid form II which is prepared as particle suspension in the formulation. Linezolid may be loaded to the delivery vehicle (i.e., hydrogel) to form suspension with about 1% to about 20%, or preferably about 2.5% to about 20% by weight or by volume of the final formulation. In some examples, the suspension formulation may comprise about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 150 mg/ml, or about 200 mg/ml linezolid.

In some embodiments, the linezolid formulation of the present invention comprises poloxamer as the delivery vehicle which forms hydrogel in responding to the temperature increase. In some aspects, the poloxamer is Poloxamer 407. The linezolid formulation of the present invention may comprise Poloxamer 407 with about 9.5% to about 17% by weight of the formulation, or about 9.5% to about 14.5% by weight of the formulation, or about 10.5% to about 13.5% by weight of the formulation, or at a concentration of about 115 mg/ml to about 207 mg/ml in the formulation, or at a concentration of about 130 mg/ml to about 165 mg/ml in the formulation. Preferably the linezolid formulation may comprise Poloxamer 407 with about 10.8% to about 12.8% by weight of the formulation, or at a concentration of about 130 mg/ml to 156 mg/ml in the formulation.

In some embodiments, the linezolid formulation of the present invention comprises a radio-opaque dye. In some aspects, the agent is iohexol. The linezolid formulation may comprise iohexol with about 14% to about 59% by weight of the formulation, or about 14% to about 40% by weight of the formulation, or at a concentration of about 165 mg/ml to about 718 mg/ml in the formulation, or at a concentration of about 200 mg/ml to about 450 mg/ml in the formulation. Preferably the linezolid formulation may comprise iohexol with about 17% to about 30% by weight of the formulation, or at a concentration of about 206 mg/ml to 364 mg/ml in the formulation.

In one preferred embodiment, the linezolid formulation comprises linezolid form II at about 2.5% to about 20% by weight or by volume of the final formulation and a delivery vehicle (aka the diluent) comprising poloxamer 407 at about 10.8% to about 12.8% by weight of the formulation and iohexol at about 17% to about 30% by weight of the formulation. The formulation is a linezolid suspension. The linezolid formulation is injectable and has a sol-gel transition temperature at about 26° C. to about 36° C.

Formulations of the present invention may be applied to a subject in need in the lumbar intervertebral disc and/or the adjacent vertebrae, ligaments, muscles, tendons and joints, and the application is carried out by open surgery or by injection or by means of a microsurgical or percutaneous technique.

In some embodiments, the present invention provides methods of manufacture and use of the linezolid formulations. In some examples, the linezolid formulation may be packed separately including a dose of linezolid powders and a solution of delivery vehicle comprising poloxamer 407 and iohexol with an optimized concentration ratio. The suspension can be prepared by mixing the linezolid power and poloxamer vehicle before administration. Provided in the present invention also includes a kit comprising the present compositions, vehicles and a syringe and/or needle for administering the sterile injectable formulation.

DETAILED DESCRIPTION OF THE INVENTION

Figure 1A:
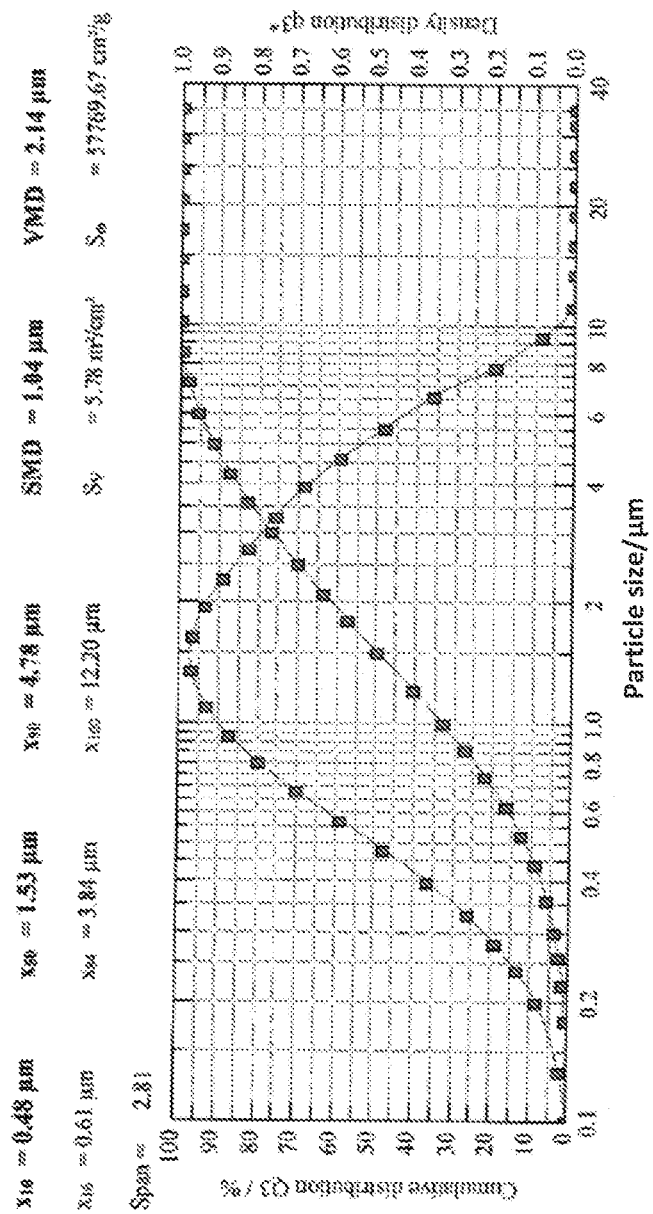
FIG. 1A depicts linezolid (form II) particle size distribution after micronisation.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The present invention is based on discoveries in human studies that chronic low back pain (CLBP) is often associated with Modic changes and disc herniation in which bacterial infection is observed. In accordance, pharmaceutical compositions and formulations comprising antibiotics against bacterial infections that cause Modic changes and CLBP are developed. These formulations and methods can be used for treating, preventing, ameliorating, and/or mitigating one or more types of pain or phenotypic presentation found to be coincident with diseases, conditions or disorders of the bones, joints, ligaments and/or tendons, especially where there is an association with Modic changes or bone edema caused by bacteria infection.

Types of pain may include, but are not limited to, acute pain, sub-acute pain, chronic or constant pain, local pain, radicular pain, referred pain, somatic pain, radiating pain, neuropathic pain, inflammatory pain, and pain of mixed or non-specific origin. Pain may present in various parts of the body including the limbs, muscles, skin, joints, deep tissues or organs, or spine (including the cervical, thoracic, lumbar or sacral spine).

Phenotypic presentations, defined as any outward manifestation, whether perceived or experienced by a subject, may include, but are not limited to any type of pain generally, disturbed sleep at night due to pain, pain during the Valsalva maneuver, pain during active flexion of the lumbar spine, pain during active extension of the lumbar spine, positive cranial compression test, pain during springing test, difficulty to turn over in bed, difficulty to get out of a chair, difficulty to get on stairs, difficulty to bend or kneel down, and difficulty to stand or walk for a long time.

Diseases, conditions or disorders of the bones, joints, ligaments and/or tendons that are coincident with pain include, but are not limited to: Modic changes, bone edema, lumbar disc herniation, tendonitis, tendon rupture, ligament inflammation, ligament rupture, symphysiolysis, pelvic girdle syndrome, and Scheuermann's disease.

The pain or phenotypic presentation may be (1) caused by the disease, condition or disorder, (2) occur at the same time as the disease, condition or disorder, (3) present at or close to the site of the disease condition or disorder, or (4) any combination of the foregoing. Examples of diseases that cause lower back pain (LBP) include arthritis, Diffuse Idiopathic Skeletal Hyperostosis (DISH or Forestier's Disease), sciatica, degenerative disc disease, lumbar spinal stenosis, spondylolisthesis, herniated disc, scoliosis, radiculopathy, joint dysfunction, coccydynia, endometriosis and osteoporosis.

The present invention relates to linezolid compositions and formulations that provide local delivery of an effective amount of linezolid to a diseased site/sites, or areas closely next to the site(s) that need to be treated. Linezolid is formulated in thermosensitive poloxamer vehicles that form degradable gels in response to the temperature changes. These thermosensitive carriers, which are aqueous solutions at room temperature, form a gel in situ at body temperature and release the carried linezolid to the target site(s). The gelling property of the formulation could avoid leaking of active drugs from the injected sites, therefore, increasing the amount of active drugs at the target sites.

I. Linezolid Formulations

Pharmaceutical compositions and formulations of the present invention comprise linezolid as the active pharmaceutical ingredient (the API) in combination with one or more pharmaceutically-acceptable carriers or excipients to treat, prevent, ameliorate, or mitigate pain. Linezolid compositions and formulations of the present invention may optionally comprise one or more additional active substances, e.g. therapeutically and/or prophylactically active substances. In some examples, the compositions may comprise at least another anti-inflammatory agent or another anti-infection agent, or the like.

Particularly the linezolid formulations may be used for administering the antibiotic compositions as discussed herein to a diseased site (or sites) for treating, preventing, ameliorating, or mitigating lower back pain and simultaneously eliminating bacterial infection in a cervical, thoracic, lumbar or sacral vertebra.

Formulations described herein may be prepared by any method known or hereafter developed in the art of pharmacology. General considerations in the formulation and/or manufacture of pharmaceutical agents may be found, for example, in Remington: The Science and Practice of Pharmacy 21st ed., Lippincott Williams & Wilkins, 2005 (the contents of which are incorporated herein by reference in their entirety). In general, such preparatory methods include the step of bringing the active ingredient into association with an excipient, a diluent and/or one or more other accessory ingredients, and then, if necessary and/or desirable, dividing, shaping and/or packaging the product into a desired single- or multi-dose unit.

A pharmaceutical formulation in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The linezolid formulation of the present invention may comprise a therapeutically effective amount of linezolid formulated in a delivery vehicle which comprise a thermosensitive poloxamer hydrogel and a non-ionic contrast agent iohexol. The delivery vehicle comprising poloxamer and iohexol is an aqueous solution below 26° C. and gels at higher temperature e.g. closer to the body temperature. Optionally one or more pharmaceutically acceptable excipients may also add to the formulation. Relative amounts of the active ingredient (i.e. linezolid), the pharmaceutically-acceptable excipient, and/or any additional ingredients in a pharmaceutical composition in accordance with the invention will vary, depending upon the identity, size, and/or condition of the subject treated and further depending upon the route by which the composition is to be administered.

The formulation may be injectable. The injectable pharmaceutical compositions are formulated to be injected to an anatomical structure of a subject, including but not limited to, an intervertebral disc, intervertebral space, intra-articular space, ligament, tendon, tendon and bone junction, joint, epidural space, facet joint, site adjacent to bone edema, or other spinal compartments. In one preferred embodiment, the injectable linezolid formulation can be used for delivering the API into the intervertebral disc and/or the intervertebral disc space. The injectable formulations comprise at least one polymer which forms a solution but gels at body temperature. The thermosensitive hydrogels carry the loaded antibiotics to the injected site, where antibiotic is effective against infections. The gelling formulation of the present invention may stay long enough in the injected place for the antibiotic to diffuse into the disc tissue, and avoid leaking of antibiotics from the injected area. This feature is particularly beneficial in damaged discs where a quite fluid administration might quickly leak out of the disc when the injection needle is withdrawn.

In some embodiments, linezolid compositions and formulations are administered to humans, human patients or non-human subjects. For example, the formulation may be administered to patients with lower back pain or to patients at risk of developing lower back pain. In some embodiments, the subject to whom the therapeutic composition is administered suffers from or is at risk of developing pain at or near a bone, a joint, a ligament, or a tendon.

Active Ingredient-Linezolid

As described in the background, chronic low back pain is often closely related to Modic changes following lumbar disc herniation. Since anaerobic bacteria are often observed in the nuclear tissues of lumbar herniated discs, pharmaceutical compositions for treating pain associated with Modic changes may comprise at least one antibiotic as an active ingredient that kills or inhibits one or more target bacteria.

Selection of active agents may depend on the bacterial pathogens isolated from Modic discs. The bacterial pathogens most frequently isolated from Modic discs are *Staphylococcus* spp. and *P. acnes*. Antibiotics resistances vary in different populations and territories worldwide. To have a robust and widely effective therapy, coverage of common resistances would be preferred with *P. acnes* and *Staphylococcus*, or with *P. acnes* only as a minimum. Preferably, antibiotics that are effective against current clinical isolates from any infection site may be selected as active agents of the present compositions and formulations, given the resistance profiles of pathogens isolated at the site of infection associated with Modic For example, pharmaceutical formulations of the present invention may comprise active agents for treating both *Staphylococcus* spp. and *P. acnes* which are the bacterial pathogens most frequently isolated form Modic discs. In some aspects, pharmaceutical formulations of the present invention may comprise at least one antibiotic for the treatment of the *P. acnes* infection that causes the majority of the investigated infection, about 38% of Modic Type 1 patients. Evidence from prior treatment with a number of potential antibacterial therapies for *P. acnes* and *Staphylococcus* spp. respectively identified several antibiotics that are effective again at least one of the pathogens. In accordance with the present invention, antibiotics that are effective against both *P. acnes* and Staphylococci may be selected as active agents of the present compositions and formulations. In some embodiments, a combination of the antibiotics that are effective against both *P. acnes* and Staphylococci may be selected.

In one preferred embodiment, the antibiotic is linezolid. Linezolid is the first clinically used oxazolidinone against most Gram-positive bacteria that cause disease, including streptococci, vancomycin-resistant *enterococci* (VRE), and methicillin-resistant *Staphylococcus aureus* (MRSA) (Gaudin et al., *Eur J Clin Microbiol Infect Dis.* 2013, 32(2):195-198). It has been used successfully for the treatment of patients with endocarditis and bacteraemia, osteomyelitis, bone and joint infections and tuberculosis and it is often used for treatment of complicated infections when other therapies have failed (Gautier et al., *JM.J Biomater Appl.* 2012, 26(7):811-828; Tsiolis et al., *Surg Infect (Larchmt).* 2011, 12(2): 131-135). Long-term use (e.g., more than 2 weeks) of linezolid could cause serious side effect (Falagas et al., *Int. J Antimic Agents,* 2007, 29(3): 233-239). Linezolid is well absorbed, with a bioavailability of approximately 100% in healthy volunteers. Linezolid can penetrate to tissues relatively fast to reach its MIC at 4 mg/L. It can also penetrate to intervertebral discs and surrounding tissues (Komatsu et al., *Eur Spine J.* 2010, 19(12): 2149-2155). Higher success rates for linezolid may occur at AUC: MIC values of 80-120 and when concentrations remain above the MIC for the entire dosing interval (reviewed by Dryden, *J. Antimicrob. Chemother.* 2011, 66 (suppl 4): iv7-iv15).

In accordance with the present invention, linezolid is selected as the active ingredient and formulated to deliver a pharmaceutically effective amount of linezolid to a target site in a subject in need. The effective amount of the compositions is provided based, at least in part, on the target bacteria, means of administration, and other determinants. In general, an effective amount of the composition provides efficient killing or inhibition of target bacteria and reduces pain or the risk of developing pain in the subject in need.

In some embodiments, an effective dosage level of linezolid is above the minimum inhibitory concentration (MIC) of the target bacteria. The target bacteria are anaerobic bacteria, such as *P. acnes, Corynebacterium propinquum*, or those of the genus *Staphylococcus*.

Different crystal modifications (polymorphs) of Linezolid can be obtained through recrystallization using organic solvents under different condition. Several polymorphic forms of linezolid can be selected as the active ingredient of the present formulations. For example, linezolid can be linezolid form I (e.g., U.S. Pat. No. 6,444,813), or form II (e.g., U.S. Pat. No. 6,559,305), or form III (e.g., U.S. Pat. No. 7,718,799; U.S. Patent publication No. 2007/0104785), or form IV (e.g., U.S. Patent Publication No. 2008/0319191), or other crystal forms as described in PCT Application Publication Nos. WO2007/026369, WO2006/110155 and WO2014/013498; and U.S. Patent Publication No. 2017/0008919; the contents of each of which are incorporated herein by reference in their entirety. As detailed in U.S. Pat. No. 6,559,305, Linezolid ((S)—N-[[3-[3-fluoro-4-(4-morpholinyl)phenyl]-2-oxo-5-oxazolidinyl] methyl] acetamide) form II may be characterized by a powder X-ray diffraction spectrum having the following peaks:

| d-Spacing (Å) | Two-Theta Angle (°) | Relative Intensity (%) |
|---|---|---|
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1 |

As detailed in U.S. Pat. No. 6,559,305, Linezolid ((S)—N-[[3-[3-fluoro-4-(4-morpholinyl)phenyl]-2-oxo-5-oxazolidinyl] methyl] acetamide) form II may be further characterised by an infrared (IR) spectrum as a mineral oil mull having the following peaks: 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852, and 758 $cm^{-1}$.

In one embodiment, Linezolid form II is selected as the active ingredient of the present formulation. Linezolid form II may be milled into small particles and uniformly dispersed in a poloxamer solution at low or room temperature. The dispersed linezolid form II particles form a suspension in the poloxamer solution.

In accordance with the present invention, linezolid particles may be sterilized for preparing sterile injectable formulations. Linezolid may be sterilized by any methods known in the art (e.g., dry heat, or steam). In a preferred embodiment, linezolid particles may be sterilized by gamma irradiation.

Companion (or drugs given in combination) drugs may be administered along with the active ingredients of the present invention. In certain embodiments, an anti-inflammatory drug is also administered, such as aspirin, ibuprofen, ketoprofen, naproxen, cefacoxib, rofecoxib, parecoxib, celecoxib, valdecoxib, and indomethacin. In certain embodiments, a pain relieving medication is also administered, such as acetaminophen, morphine, oxycodone, and codeine. Companion drugs may also include over-the-counter pain relieving patches, drugs and/or ointments.

Delivery Vehicle-Thermosensitive Hydrogels

The active ingredient of the invention (i.e., linezolid) may be incorporated into a delivery vehicle for administration to a subject in need. The delivery vehicle may be suitable for injection. For example, the delivery vehicle may be an aqueous solution, a low viscous solution, a suspension, or a reversible thermogel. The vehicle preferably is a biodegradable and biocompatible carrier. As used herein, the term "biocompatible" means the carriers are not toxic to the tissues and cells. As used herein, the terms "biodegradable" and "bioabsorbable" are used interchangeably. The biodegradation or bioabsorbance in the context of the present invention refers to the degradation, disassembly, digestion or disappearance of the delivery materials after releasing formulated therapeutically active ingredients, in the biological environment through the action of living organisms and most notably at physiological pH and temperature. Specific reactions include but are not limited to chemical or enzymatic degradation.

In accordance with the present invention, thermosensitive hydrogels biomaterials especially injectable thermosensitive hydrogels with solution-gel transition temperature around or below physiological temperature are used in linezolid delivery. An aqueous suspension comprising linezolid is formed at room temperature but after in vivo injection, can transit into a non-flowing/stiff gel at body temperature. Over several hours or days, the gels break down (i.e. biodegradable). Varying the concentrations of components in the formulation can allow fine tuning of the properties, such the temperature at which the gel forms or the rate of degradation of the gel.

1. Poloxamer

Thermosensitive hydrogel may be made up by synthetic polymers, natural polymers or a combination thereof. The pharmaceutical agents (e.g. linezolid) and appropriate carriers may be mixed with the polymer solutions in vitro prior to gelation and the drug-loaded hydrogel can form in situ after in vivo administration.

In some embodiments, the thermosensitive hydrogel may be formed by synthetic polymers. The synthetic polymers may include, but are not limited to, poly(ethylene oxide)-poly(propylene oxide)-poly(ethylene oxide) (PEO-PPO-PPO) triblock copolymers (also known as Poloxamers® or Pluronics®) and derivatives thereof, poly (N-isopropylacrylamide) based (PNIPAAM) copolymers and derivatives thereof, poly(organophosphazene), and poly(ethylene glycol) (PEG)/biodegradable polyester copolymers.

Poloxamers® or Pluronics® are FDA-approved thermosensitive synthetic polymers. Poloxamers are nonionic triblock copolymers composed of a central hydrophobic chain of polyoxypropylene (poly(propylene oxide)) flanked by two hydrophilic chains of polyoxyethylene (poly(ethylene oxide)). Biocompatible Poloxamers have been widely used for drug delivery and tissue engineering. Poloxamer-based hydrogels allow reversible gelation under certain physiological temperature and pH by adjusting the composition of PEO and PPO, and the overall molecular weight and concentration. The Poloxamers that have been used for drug delivery include, but are not limited to, Poloxamer® 188 (Pluronic® F-68, FLOCOR or RheothRx), Poloxamer® 237 (Pluronic® F87), Poloxamer® 238 (Pluronic® F.-88), Pluronic® F-98, Poloxamer® 124 (Pluronic® L-44), Poloxamer® 184 (L-64), Poloxamer® 338 (Pluronic® F-108), Poloxamer® 401 (Pluronic® L-121) and Poloxamer® 407 (Pluronic® F-127). The physicochemical characteristics and gel-forming properties of some selected Poloxamers can be found in Table 1 from U.S. Pat. No. 5,702,717; the contents of which are herein incorporated by reference in their entirety.

Poloxamer® 407 (also known as Pluronic® F-127, Kolliphor 407, and SynperonicPE/F 127) is one of the least toxic of the block copolymers and has been used extensively as drug delivery systems. At a concentration of pure 20% (w/w), Poloxamer® 407 is liquid in an aqueous solution at or below room temperature (~25° C.), but forms a soft gel at body temperature (37° C.). Poloxamer® 407 is triblock copolymer consisting by weight of approximately 70% PEO (polyethylene glycol) and 30% PPO (polypropylene oxide) with an average molecular weight of 11500. Like other Poloxamers, Poloxamer® 407 exhibits thermoreversible gelation behavior. Poloxamer® 407 has been employed for the delivery of many drugs, proteins and genes, as reviewed in Gong et al. (*Curr. Med. Chem.* 2013, 20, 79-94; the contents of which are herein incorporated by reference in their entirety).

In some embodiments, the thermosensitive hydrogel may be formed by natural polymers including modified polymers with improved the thermoresponsive gelation behavior. The natural polymers that may be used to form thermosensitive hydrogels include, but are not limited to, chitosan and related derivatives, methylcellulose, alginate, hyaluronic acid, dextran, and xyloglucan.

2. Non-Ionic Contrast Agent-Iohexol

Though previous research indicates the poloxamer entrapped antibiotics including vancomycin and linezolid can be used for controlled and sustained release of antibiotics to increase its effectiveness in inhibiting bacterial proliferation (Veyries et al., *Int. J Pharm.*, 1999, 192(2): 183-193; Veyries et al., *Antimicrob Agents Chemother.*, 2000, 44(4):1093-1096; Kalorewicz et al., *Polim. Med,* 2011, 41(4) 3-15; and Lee et al., J Control Release, 2004, 96(1): 1-7), none of these previous studies investigate the effect of addition of other pharmaceutical agents. For example, radiopaque contrast agents are often used as a guide to confirm needle tip placement, during injections and other pain procedures (e.g., discography). The iodine content in the contrast agent such as iohexol (Trade name: Omnipaque) can block penetration of x-rays and visualize the injection sites under fluoroscopy or X-ray. Iohexol is a triiodinated molecule having a molecular weight of 821.1 (46.3% iodine content). The most commonly available iohexol agent Omnipaque has different iodine concentrations, for example, Omnipaque 140 contains 302 mg iohexol equivalent to 140 mg of organic iodine per mL; Omnipaque 180 contains 388 mg iohexol equivalent to 180 mg of organic iodine per mL; Omnipaque 240 contains 518 mg iohexol equivalent to 240 mg of organic iodine per mL; Omnipaque 300 contains 647 mg iohexol equivalent to 300 mg of organic iodine per mL; and Omnipaque 350 contains 755 mg iohexol equivalent to 350 mg of organic iodine per mL.

In accordance with the present invention, the poloxamer containing vehicle may further comprise a radiocontrast agent such as iohexol to facilitate the application of the linezolid formulation to a target disease site, for example, an intervertebral disc. The addition of a radiocontrast agent in the present antibiotic formulations will assist a clinic practitioner (like a physician) to see the product being administered, and monitor the condition of the disc being administered using fluoroscopy. This real-time information can help the practitioner to decide when to stop injection when the disc is full and is starting to leak.

Figure 2:
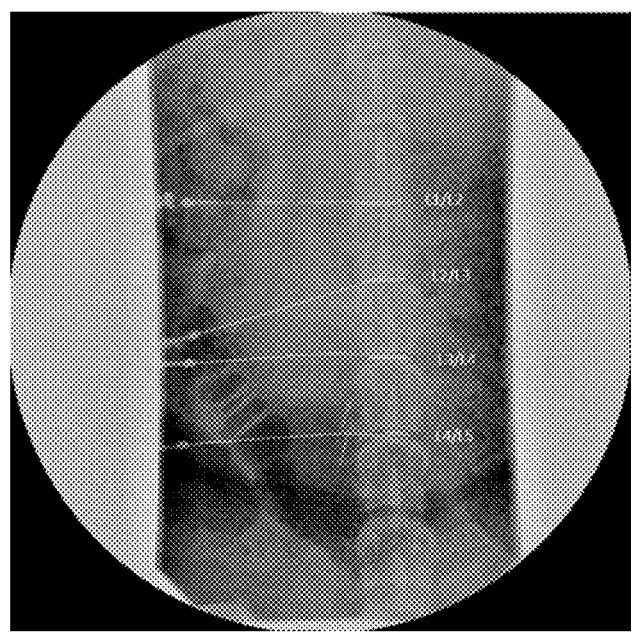
FIG. 2 is an image that shows needles positioned into adjacent discs and 0.1 ml of iohexol containing formulation injected. The position of the injected formulation can be observed using x-ray or fluoroscopy imaging.

Experiments conducted in the present invention indicated that the addition of iohexol to the linezolid formulations increases the radiographic visibility of the composition for monitoring its delivery to the diseased sites (e.g., as shown in FIG. 2). It was also found that the concentrations of iohexol and poloxamer 407 in the delivery vehicle need to be optimized to achieve the target temperature range for the solution to gel transition of the present thermosensitive hydrogel formulations (see Example 5). The interaction of poloxamer and iohexol in the hydrogel affects the transition temperature of the linezolid formulation.

In some embodiments, the delivery vehicle comprising poloxamer 407 and iohexol may be prepared as separate solution prior to addition of linezolid to form the linezolid formulation (i.e. linezolid suspension). The concentrations of poloxamer and iohexol are optimized to certain ranges so that the gelation temperature of the solution is optimized at or close to the body temperature.

The present invention also provides thermosensitive hydrogels for drug delivery. In some embodiments, the vehicle may comprise poloxamer as a pharmaceutically acceptable biodegradable and biocompatible polymer which forms hydrogel in responding to the temperature increase. In some aspects, the delivery vehicle comprises Poloxamer 407 with about 10% to about 17% by weight of the delivery vehicle, or at a concentration of about 121 mg/ml to about 207 mg/ml by volume of the vehicle. Preferably it may comprise Poloxamer 407 with about 11.5% to about 13.5% by weight of the vehicle, or at a concentration of about 140 mg/ml to 165 mg/ml in the vehicle. In other embodiments, the delivery vehicle further comprises a radio-opaque dye. In some aspects, the vehicle comprises iohexol with about 14.5% to about 62.5% by weight of the vehicle, or at a concentration of about 174 mg/ml to about 755 mg/ml in the vehicle. Preferably the delivery vehicle may comprise iohexol with about 18% to about 35% by weight of the vehicle, or at a concentration of about 206 mg/ml to 425 mg/ml in the vehicle.

As one skilled in the art could know that in addition to form the linezolid suspension of the present invention, the delivery vehicle as described herein can be used to deliver any drug, for example an antibiotics from antibiotic classes of beta-lactams (e.g., penicillins, cephalosporins, carbapenems, and monobactams), oxazolidinones, aminoglycosides, glycopeptides, lipopeptides, and glycylcyclines.

In accordance with the present invention, the poloxamer hydrogel solution may be made at a lower temperature comprising the steps of (1) preparing a cold iohexol solution by adding iohexol to a solution comprising tromethamine and calcium disodium EDTA (pH at about 8.0); and (2) adding poloxamer 407 powder slowly to the cold iohexol solution and stirring the solution until the poloxamer powder is completely dissolved, wherein the poloxamer powder is added as portions. The poloxamer-iohexol solution may be sterilized and packed into separate vials.

Other Carriers and Excipients

Linezolid formulations of the present invention may further comprise one or more pharmaceutically-acceptable excipients, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, a pharmaceutically-acceptable excipient may be at least 95%, at least 96%, at least 97%, at least 98%, at least 99%, or 100% pure. In some embodiments, an excipient may be approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

In some embodiments, the formulation of the present invention may further comprise chelating agents and buffering agents. Exemplary chelating agents include ethylenediaminetetraacetic acid (EDTA), citric acid monohydrate, disodium edetate, disodium calcium edetate, dipotassium edetate, edetic acid, fumaric acid, malic acid, phosphoric acid, sodium edetate, tartaric acid, and/or trisodium edetate. In one example, the agent may be a salt of EDTA.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof. In one embodiment, the buffering agent may be tromethamine.

Linezolid Formulations

The linezolid formulations of the present invention comprise a thermosensitive poloxamer hydrogel loaded with an effective amount of linezolid, a non-ionic contrast agent iohexol at a concentration which is optimized for the poloxamer solution to gel transition, and optionally one or more pharmaceutically acceptably excipient.

In some embodiments, linezolid may be prepared as a suspension in a delivery vehicle comprising poloxamer and iohexol. In one preferred embodiment, the API (i.e., linezolid) is linezolid Form II, which is milled to form small particles and sterilized by gamma irradiation, and forms a suspension in poloxamer-iohexol vehicles.

In some embodiments, formulations of the present invention comprise linezolid at a concentration ranging from about 1% to 50% by weight or by volume of the composition (i.e., the linezolid suspension). In some aspects, it may be loaded with about 1% to about 20%, or about 2.5% to about 20% or about 2.5% to about 10%, or about 3.0% to about 10% by weight or by volume of the composition. In one aspect, the linezolid formulation may comprise about 2.5%, 5%, 7.5%, 10%, 12.5%, 15%, 17.5% or 20% linezolid by weight of the final composition (e.g., a suspension). Linezolid may be present in the formulation at a concentration from about 10 mg/ml to about 200 mg/ml, or from about 20 mg/ml to about 200 mg/ml, or from about 50 mg/ml to about 200 mg/ml. Particularly linezolid may be present in the formulation at a concentration of 10 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 100 mg/ml, 150 mg/ml, or 200 mg/ml.

In some embodiments, the formulation of the present invention comprises poloxamer as a pharmaceutically acceptable biodegradable and biocompatible polymer which forms hydrogel in responding to the temperature increase. In some aspects, the poloxamer is Poloxamer 407. The linezolid formulation of the present invention may comprise Poloxamer 407 with about 9.5% to about 17% by weight of the formulation, or about 9.5% to about 14.5% by weight of the formulation, or at a concentration of about 115 mg/ml to about 207 mg/ml, or at a concentration of about 115 mg/ml to about 173 mg/ml in the formulation. Preferably the linezolid formulation may comprise Poloxamer 407 with about 10.8% to about 12.8% by weight of the formulation, or at a concentration of about 130 mg/ml to 156 mg/ml in the formulation.

Pharmaceutical formulations of the present invention further comprise a non-ionic contrast agent. By way of example, a pharmaceutical formulation according to the present invention may comprise about 30 mg to about 600 mg iodine per milliliter of the formulation solution, preferably about 50 mg to about 300 mg, or about 75 mg to about 200 mg iodine per milliliter of the formulation solution.

In some aspects, the agent is iohexol. The pharmaceutical compositions may comprise iohexol with about 14% to about 59% by weight of the formulation, or at a concentration of about 165 mg/ml to about 718 mg/ml in the formulation. Preferably the linezolid formulation may comprise iohexol with about 17% to about 30% by weight of the formulation, or at a concentration of about 206 mg/ml to 364 mg/ml in the formulation.

Other surfactants, solvents or co-solvents known to those of skill in the art may also be used in some embodiments within the scope of the invention.

In some embodiments, the linezolid formulation of the present invention comprises about 1% to about 20% linezolid by weight of the formulation (w/w), about 9.5% to about 17% poloxamer 407 by weight of the formulation (w/w), and about 14% to 59% iohexol by weight of the formulation (w/w). In one preferred embodiment, the linezolid formulation comprises about 5% w/w linezolid, about 11.8% w/w poloxamer and about 27.2% w/w iohexol. In some examples, the aqueous formulation may gel at about 26° C., or about 27° C., or about 28° C., or about 30° C., or about 31° C., or about 32° C., or about 33° C., or about 34° C., or about 35° C., or about 36° C., or about 37° C. In one non-limiting example, the linezolid formulation gels at about 28° C. Linezolid can diffuse from the stiff gel. Over several days the gels breakdown. Varying the concentrations of components (e.g., iohexol and poloxamer 407) in the formulation can allow fine tuning of the properties of the gels such as solution-to-gel transition temperature.

In some embodiments, the formulation may be prepared by a method comprising the steps: (a) milling linezolid form II powder to form small linezolid particles; (b) preparing a unit of linezolid particles from step (a) and sterilizing the preparation; (c) preparing a delivery vehicle comprising poloxamer 407 and iohexol; and (d) suspending said linezolid particles from step (b) in the delivery vehicle from step (c) to form a stable and homogeneous suspension.

The thermogel poloxamer can be dissolved in an appropriate volume of an aqueous solution at low temperature and the concentrations of poloxamer and iohexol are optimized in terms of the gelation feature of the delivery vehicle.

Linezolid, particularly linezolid Form II, may be milled to form small particles using dry air-jet milling, or any other milling approaches. The resulted linezolid powder may be further sterilized by dry heating and/or gamma irradiation.

In some embodiments, the linezolid particles and the poloxamer/iohexol delivery vehicle may be prepared and packed separately, for instance, in two separate vials. The two preparations can be mixed to form a linezolid suspension before administration. Prior to the application, the linezolid powder and the vehicle are mixed to form a homogeneous suspension. The antibiotic suspension may be taken up into a syringe and prepared with the intended dose volume. In one example, about 253 mg linezolid powder may be provided in the vial and about 7 ml of delivery vehicle comprising poloxamer and iohexol may be prepared in the other vial. The delivery vehicle may be provided at a volume from about 3.8 to about 5.8 ml, or from about 4.6 ml to about 5.0 ml.

Injectable formulations can be sterilized, for example, by filtration through a bacterial-retaining filter, by irradiation, by steam sterilization, and/or by incorporating sterilizing agents in the form of sterile solid compositions which can be dissolved or dispersed in sterile water or other sterile injectable medium prior to use.

In some embodiments, thermosensitive hydrogel formulations of the present invention may be administered to a disease site using a needle. The feature of the water solubility of thermogels at room temperature, and the relatively low viscosity of the aqueous solution makes the use of small-bore needles possible. Such injectable formulation can be effectively administered to a patient with a small size needle without exhibiting pre-gelation.

II. Administration and Dosing

The linezolid compositions of the present invention may be administered by any route which results in a therapeutically effective outcome. In one preferred embodiment, the formulation is suitable for injection. Injectable administration producing a localized effective level of linezolid (above MIC of target bacteria) has beneficial outcomes (e.g., pain relief).

Injectable administration would reduce the level of systemic side effects, increase patient compliance to the dosing regime and increase efficacy at the site of action with a smaller antibiotic dosage. The advantages may include relative ease of application, localized delivery for a site-specific action in the body, reduced dosing frequency without compromising the effectiveness of the treatment, increased dosing compliance, etc.

Pharmaceutical compositions in accordance with the invention are typically formulated in dosage unit form for ease of administration and uniformity of dosage. It will be understood, however, that administration of the pharmaceutical compositions of the present invention will be decided by the attending physician within the scope of sound medical judgment.

In accordance with the present invention, the pharmaceutical formulation may be administered at dosage levels sufficient to deliver a total dose of 5 mg to 450 mg of linezolid to the intervertebral disc, to obtain the desired therapeutic effect. In some embodiments, the compositions may deliver about 50 mg to about 200 mg of linezolid to obtain the desired therapeutic effect. In some embodiments, the total dose is about 10 mg to about 100 mg of linezolid, or about 10 mg to about 200 mg of linezolid, or about 20 mg to about 200 mg, or about 50 mg to about 200 mg of linezolid. In some examples the formulation may deliver a total dose of 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg, of linezolid. In some embodiments, the dosage level is determined based upon the infected discs. For example, dosages may range from 5 mg to 450 mg for each infected disc, for example, 5 mg for each infected disc, or 10 mg for each infected disc, or 15 mg for each infected disc, or 20 mg for each infected disc, or 50 mg for each infected disc, or 100 mg for each infected disc, or 150 mg for each infected disc, or 200 mg for each infected disc, or 250 mg for each infected disc, or 300 mg for each infected disc, or 350 mg for each infected disc, or 400 mg for each infected disc, or 450 mg for each infected disc for each infected disc. In one preferred embodiment, the effective amount of linezolid is about 50 mg to about 200 mg for each infected disc.

As non-limiting examples, the present linezolid suspension may be administered at a volume range from about 0.1 ml to about 4.0 ml, for example, 0.1 ml, or 0.3 ml, or 0.5 ml, or 1.0 ml, or 1.2 ml, or 1.5 ml, or 2.0 ml, or 2.5 ml, or 3.0 ml, or 3.5 ml, or 4.0 ml, or 4.5 ml, or 5.0 ml to achieve the expected total dose of linezolid for each infected disc.

In some embodiments, a single administration (e.g., a single injection) is used to deliver a desired dosage of linezolid to the infected disc. In other embodiments, multiple administrations may be used to obtain the desired therapeutic effect. As non-limiting examples, a second dose, maybe a third dose is administered 2 days, or 5 days, or 10 days, or two weeks, or three weeks, or one month after the previous dose.

In some embodiments, the formulations of the present invention may be administered to a subject in need at or near the bone, joint, ligament and tendon by a single injection, or alternatively through multiple injections at more than one site. For instance, the linezolid formulation may be injected into multiple vertebra discs from the same side of the spine, or from both sides of the spine. In other examples, formulations and compositions of the present invention may be injected into vertebra discs and vertebra disc space.

III. Kits, Needles and Devices

In accordance with the present invention, kits comprising the linezolid formulation of the present invention are also provided. In some embodiments, the kit may comprise one or more dose units of linezolid powder; and a hydrogel vehicle comprising poloxamer and iohexol, wherein the linezolid powder and the hydrogel vehicle can be mixed to form the linezolid suspension for use.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

Devices for administration may be employed to deliver pharmaceutical compositions comprising at least one antibiotic of the present invention according to single, multi- or split-dosing regimens taught herein. According to the present invention, these multi-administration devices may be utilized to deliver the single, multi- or split doses of antibiotics loaded in the formulations contemplated herein.

In some embodiments, devices for delivering medical agents have been described by Mckay et al. and are taught for example in PCT Patent Publication NO.: WO2006/118804, the contents of which are incorporated herein by reference in their entirety. According to Mckay, multiple needles with multiple orifices on each needle are incorporated into the devices to facilitate regional delivery to a tissue, such as the interior disc space of a spinal disc.

Syringes using needles may be employed to administer the pharmaceutical formulations of the present invention. In some cases, the needle tips may be specialized for a particular injection purpose, such as spinal injection. Syringes for spinal injection may have a needle placed into a structure or space in the spine. The needle may have a bevel of any types from Quincke babcock, Sprotte, Whitacre, Greene, Pitkin and Tuohy. The shaft of the needle may be straight or curved, and be in a certain length suitable for placing the medications in a specific location in the spine. For examples. The syringe and needles may be designed as disclosed in U.S. Pat. Nos. 5,628,734; 6,500,153; 7,367,961; and 8,112,159; the contents of each of which are incorporated herein by reference in their entirety.

In some embodiments, the syringes and needles for administration of the pharmaceutical formulations of the present invention may contain special structures configured for mixing the components of the pharmaceutical formulations in situ. The syringe may include one, two, or more separate chambers in which the components of the pharmaceutical formulations are stored separately and are mixed right before the injection.

Definitions

Active pharmaceutical ingredient (API): As used herein, the term "active pharmaceutical ingredient (API)" refers to a pharmaceutical agent that is biologically active. For example, a substance that when is administered to an organism, has a biological effect on that organism, is considered to be biologically active. In accordance with the present invention, the API is linezolid.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Formulation: As used herein, a "formulation" includes at least an active ingredient and a delivery agent.

Hydrogel: As used herein, the term "hydrogels" are viewed as water insoluble, crosslinked, three-dimensional networks of polymer chains plus water that fills the voids between polymer chains. Crosslinking facilitates insolubility in water and provides required mechanical strength and physical integrity. Hydrogel is mostly water (the mass fraction of water is much greater than that of polymer). The ability of a hydrogel to hold significant amount of water implies that the polymer chains must have at least moderate hydrophilic character.

Patient: As used herein, the term "patient" refers to a subject who may seek or be in need of treatment, requires treatment, is receiving treatment, will receive treatment, or a subject who is under care by a trained professional for a particular disease or condition.

Pharmaceutical composition: As used herein, the phrase "pharmaceutical composition" refers to a composition that alters the etiology of a disease, disorder and/or condition.

Pharmaceutically acceptable: As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: As used herein, the phrase "pharmaceutically acceptable excipient" refers any ingredient other than the compounds described herein (for example, a vehicle capable of suspending or dissolving the active compound) and having the properties of being substantially nontoxic and non-inflammatory in a patient.

Site: As used herein, the term "site", when used with respect to bone edema or Modic changes, means the site of bone edema or Modic change itself or an environment 0.5-1 inch around all directions of the bone edema.

Split dose: As used herein, a "split dose" is the division of single unit dose or total treatment dose into two or more doses.

Therapeutically effective amount: As used herein, the term "therapeutically effective amount" means an amount of an agent to be delivered (e.g., antibiotic, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Therapeutically effective outcome: As used herein, "therapeutically effective amount" means an amount of an agent to be delivered (e.g., antibiotic, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Total treatment dose: As used herein, a "total treatment dose" is an amount given or prescribed in a treatment period. It may be administered as a single unit dose.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Vehicle: As used herein, the terms "vehicle" and "delivery vehicle" are used interchangeably, which refer to any agent, compound, or any combination thereof that can be used to carry an active ingredient (e.g., the API of the present invention) and deliver the same to a designated site.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

EXAMPLES

Example 1: A Sheep Model of *S. aureus* Intradiscal Infection

A sheep model of *S. aureus* intradiscal infection has been developed to test the in vivo efficacy of antibiotic formulations. Male Charollais or Suffolk cross sheep, approximately 35-40 kg at the start of the study were housed according to Home Office guidelines under the Animals (Scientific Procedures) Act 1986 and acclimatised for at least 7 days with straw bedding and access to water. They were fed a Sheep concentrate diet without added antibiotics with additional forage (hay/straw) provided.

1.1 *Staphylococcus aureus* Infection

The bacterial inoculum (ATCC 29213) was prepared from frozen glycerol/phosphate-buffered saline stock at $2.5 \times 10^6$ CFU/ml by dilution to $2 \times 10^4$ CFU/ml.

1.2 Preparation of the Formulations for Injection 0.2 ml of the *S. aureus* suspension or test formulations were drawn up into the 1 ml syringe using an 18 G 1 inch or 1.5 inch needle. The syringe may be drawn back and forth to remove bubbles as necessary. The needle was then replaced with a 25 G 4.69 inch administration needle, and primed leaving a dose of 0.05 ml or 0.1 ml. If not used immediately, the primed syringe was left in the fridge, but should be used within 30 minutes.

In a therapeutic model, each sheep was anesthetised. As part of the anaesthesia the animal was given analgesics (intra-muscular) in the form of meloxicam at the recommended dosage. This analgesic may be repeated if considered necessary by the named veterinary surgeon. Each sheep was given four 0.05 ml (target volume) intradiscal Injections at L1/L2, L2/L3, L3/L4 and L4/5 of *S. aureus* inoculum ($1 \times 10^3$ cells/disc), one injection per disc.

Approximately 1 hour, or at another selected time, after the first injection, each sheep was given a second injection of the linezolid formulation or control formulation. Each disc that was previously successfully injected with bacteria is given a 0.1 ml (target volume) intradiscal injection. The time between administration of the antibiotic and bacteria may be hours, days, weeks or months.

1.3 Injection Technique: Therapeutic Dosing.

Co-Localised Dosing

A single 20 G 3.5 inch spinal needle was positioned directly into the edge of the nucleus pulposus of each disc. Following confirmation of positioning of the needles a second 25 G 4.69 inch needle primed with the dose solution is inserted into the first needle and the tip placed into the middle of the nucleus pulposus. Following confirmation of positioning of the second needles each disc was injected with the bacteria. The inner needles will then be removed. Just prior to the 1 hour post-dose bacteria time-point a new 25 G 4.69 inch needle, primed with the dose solution, was inserted into the 20 G 3.5 inch and positioned into the middle of the nucleus pulposus. The second treatment was dose given via this needle, 1 hour post the first dose.

Discreet Dosing

Bacterial infection: A single 20 G 3.5 inch spinal needle was positioned directly into the edge of the nucleus pulposus of each disc. Following confirmation of positioning of the needles a second 25 G 4.69 inch needle primed with the dose solution was inserted into the first needle and the tip placed into the middle of the nucleus pulposus. Following confirmation of positioning of the second needles each disc was injected with the bacteria. The needles were then removed. The animals were repositioned to access the other side of the spine.

Injection of formulation: A second 20 G 3.5 inch spinal needle was positioned directly into the edge of the nucleus pulposus on the opposite side to the first injection of each disc. Just prior to time-point for administration a new 25 G 4.69 inch needle, primed with the dose solution, was inserted into the 20 G 3.5 inch and positioned into the middle of the nucleus pulposus. The second treatment dose was given via this needle.

For each injection, the individual dosing syringe was weighed, and the weight recorded, pre and post-dosing to calculate the actual dose administered.

For each formulation the dose was given slowly, this should take 30 to 60 seconds to deliver, using enough force to successfully deliver the dose to the dose without causing any dose solution to leak out at the syringe/needle joint.

A digital x-ray imaging system was used to aid injection and capture image records just prior to and post-dose. The animals were continuously monitored and when fully recovered returned to their pen.

1.4 Digital X-Ray Imaging

Each sheep was imaged and the image captured, just prior to and immediately after each dosing. Details of the sequences were recorded. A visual assessment of each IVD injection, immediately post-dose, was performed by a competent person. The injections are scored/recorded as either:

Good no leakage: good discrete dose visible within the disc, no dose visible outside of disc.

Minimal leakage: good discrete dose visible within the disc, minimal dose visible outside of disc.

Moderate leakage: reduced dose visible within the disc, dose obviously visible outside of disc.

Major leakage: minimal dose visible within the disc, majority of media obviously visible outside of disc.

In order to ensure scientific robustness in the study ideally, four treated disc/group and a minimum three/group are required. After completing the injections for the sheep, the scores are reviewed. If less than the ideal number of discs in total are scored as "good no leakage" or "minimal leakage", the addition of extra sheep to this group, up to a maximum of 2 sheep, will be considered.

1.5 Tissue Samples

At set time-points post-dose the sheep is killed. The injected vertebrae discs are dissected out and the nucleus pulposus from each disc is removed. In addition, an extra untreated disc is sampled to provide control tissue. The disc is removed after all of the treated discs for the particular animal with care to ensure no contamination between control and treated samples.

1.6 Linezolid Extraction

Extraction of linezolid from disc samples was achieved by addition of 3 ml of phosphate-buffered saline (PBS) to the pre-weighed disc samples. The mixtures were homogenized using an Omni-Prep Bead Ruptor at 4° C. A further 3.5 ml of PBS was added and the samples hand homogenised and finally another 3.5 ml of PBS added and thoroughly mixed, providing a total volume of 10 ml of PBS disc mixture. Representative aliquots of this disc homogenate containing the linezolid were diluted with disc homogenate from untreated discs to ensure that samples were within the calibration range of the analysis. The samples were extracted by protein precipitation with three volumes of acetonitrile containing tolbutamide and labetalol as internal standards (at 50 and 25 ng/ml), acidified with 0.1 ml formic acid.

After vortex mixing and centrifugation at 4° C., the supernatants were mixed with acetonitrile: water (1:1 v/v) acidified with 0.1% formic acid in a shallow well 96-well plate. The plate was sealed and shaken to ensure homogeneity prior to analysis. Samples were assayed for linezolid by positive electrospray LC-MS/MS using a Waters TQS mass spectrometer (Conditions below), against a series of matric matched calibration and quality control standards. The standards were prepared by spiking aliquots of diluted disc homogenate from untreated discs with linezolid and extracting as described above.

TABLE 1

Experimental conditions

| Instrument Information | |
|---|---|
| Instrument | Waters TQS C |
| Ionisation | ESI+ |
| Mode | MRM |
| MS conditions | |
| Capillary (kV) | 0.7 |
| Desolvation Temperature (° C.) | 600 |
| Cone gas (L/hr) | 150 |
| Desolvation gas (L/hr) | 1200 |
| Resolution mode | Unit |
| MS1 Resolution | 0.75 |
| MS2 Resolution | 0.75 |
| LC Conditions | |
| Parameter | Setting |
| Column | Acquity UPLC BEH C18 1.7 uM 2.1 × 50 mm |
| Column temperature | 40° C. |
| Flow rate | 0.8 ml/min |

TABLE 1-continued

| Experimental conditions | | |
|---|---|---|
| Injection volume | 3 ul | |
| Mobile phase A | 0.1% Formic Acid in water (v/v) | |
| Mobile phase B | 0.1% Formic Acid in acetonitrile (v/v) | |
| Gradient profile | Time (minutes) | Mobile phase B (%) |
| | 0 | 2 |
| | 0.25 | 2 |
| | 0.5 | 50 |
| | 1 | 98 |
| | 1.75 | 98 |
| | 2.6 | 2 |
| Retention time | Linezolid | 0.72 minutes |

| Compound transitions | | | | | | |
|---|---|---|---|---|---|---|
| Compound | Parent (m/z) | Daughter (m/z) | Auto-dwell | Dwell | Cone (V) | Collision (V) |
| Tolbutamide | 271.16 | 172.14 | 1 | 0.019 | 10 | 10 |
| Labetalol | 329.24 | 162.24 | 1 | 0.019 | 50 | 34 |
| Linezolid_a | 725.43 | 144.09 | 1 | 0.019 | 38 | 14 |
| Linezolid_b | 725.43 | 241.97 | 1 | 0.019 | 38 | 50 |

Pharmacokinetic analysis was performed with Phoenix WinNonL in Software version 6.4 using mean animal data of the four discs from each animal, non-compartmental analysis and uniform weighting, nominal time points and the actual amount of linezolid administered to the discs. Data points were excluded from the pharmacokinetic analysis if the dosing was considered less than nominal e.g. major leakage was observed.

1.7 Extraction and Enumeration of *S. aureus* from Sheep Disc

The nucleus of each disc was placed in a 7 mL plastic Precellys bead-beater tube containing 2 mL sterile phosphate-buffered saline (PBS) or a 6 mL plastic Sterilin bijoux. Homogenisation of each disc nucleus, to the extent that it was achievable, was performed twice in a Precellys 24BB bead-beater at 6500 rpm for 45 seconds, with a 30-second rest period between each homogenization step. Samples (approximately 100 μL) were removed and 10-fold serially diluted in sterile PBS before plating onto Mannitol Salt Agar (MSA; Thermo Scientific CM0085) by either spreading or the Miles and Misra method (https://en.wikipedia.org/wiki/Miles_and_Misra_method). MSA plates were incubated in ambient air at 37° C. for approximately 16 hours and the viable count of *S. aureus* (ATCC 29213) was determined.

Example 2: Methods for Assessing the Stability of Linezolid in Formulation Preparations Ultra Performance Liquid Chromatography (UPLC) was used to assay for the quantity and stability of linezolid in formulation preparations. Analysis was performed on a Waters Acquity system equipped with a diode array detector and single quad mass spectrometer using MassLynx software. The details of the method are listed below in Table 2.

TABLE 2

| UPLC for assaying Linezolid | |
|---|---|
| Column | BEH C18 1.7 u 100 × 2.1 mm |
| Column temperature | 40° C. |
| Injection | 1 ul |
| Detection | UV Diode array 200-500 nm |

TABLE 2-continued

| UPLC for assaying Linezolid | | |
|---|---|---|
| Phase A | 0.1% Formic acid in water | |
| Phase B | 0.15 Formic acid in acetonitrile | |

| | Time (Minutes) | | |
|---|---|---|---|
| Flow rate 0.4 ml/min | | % Phase A | % Phase B |
| | 0 | 95 | 5 |
| | 0.4 | 95 | 5 |
| | 6 | 5 | 95 |
| | 6.8 | 5 | 95 |
| | 7.0 | 95 | 5 |
| | 8.0 | 95 | 5 |

Example 3: Methods for Analyzing the Quantity of Iohexol in Formulation Preparations HPLC was used to estimate purity and quantity of iohexol in formulation preparations. The details of the method used are listed below in Table 3.

TABLE 3

| HPLC for assaying iohexol | | | |
|---|---|---|---|
| Parameter | HPLC method | | |
| Column | ACE Excel C18 Amide (100 × 1.2 mm, 1.7 um) | | |
| Column temp | 40° | | |
| Flow rate | 0.23 ml/min | | |
| Mobile Phase A | HPLC water | | |
| Mobile phase B | HPLC water:acetonitrile 1:1 v/v | | |
| Gradient | Time (min) | A (% v/v) | B (% v/v) |
| | 0 | 90 | 10 |
| | 2 | 90 | 10 |
| | 5 | 10 | 90 |
| | 7.5 | 10 | 90 |
| | 7.6 | 90 | 10 |
| | 15 | 90 | 10 |
| Injection vol. | 0.4 ul | | |
| Run time | 15 min | | |
| UV | 254 nm | | |
| PDA | 180 to 300 nm | | |
| Wash/purge solvent | Mobile phase B | | |
| Diluent | HPLC water:acetonitrile (95:5 v/v) | | |

Example 4: Linezolid Suspension Preparation 4.1. AirJet Milling of Linezolid Form II and Form III To evaluate the ability to develop linezolid suspensions with linezolid loadings of 50 and 200 mg/mL, the short term physical stability of formulations was assessed, including particle size, polydispersity and homogeneity. Different concentrations of poloxamer 407 were then added and sol-gel transition temperature and injectability/syringeability of the suspension were evaluated.

Different crystal forms of linezolid were chosen and tested for their feasibility of suspension. Two crystal modifications (polymorphs) of Linezolid: Form II (FII) and Form III (FIII) were obtained from Symed labs Ltd (India). Approximately, 1 g each of FII and FIII was jet milled using a LaboMill jet miller (F.P.S. Food and Pharma Systems s.r.l, Italy) with an injection line pressure at 7 bar and the grind line at 4 bar. The particle size distribution of the raw and air-jet milled material was analyzed by laser diffraction (Sympatec GmbH, Helos Disperse). 5 mg of each sample was placed in a dry powder disperser (RODOS/M). A reference measurement was taken before running each sample for 5 sec at 2% optical concentration. The results were obtained at a pressure of 3 bars using lenses, R1 (0.18-0.35 μm) and R2 (0.25/0.45-87.5 μm) (Table 4). The data was collected using HELOS sensor and analyzed using Window5 software.

TABLE 4

Particle size distribution of raw and jet milled FII and FIII

| API | Processed | Particle size distribution (μm) Method: Lens- $R_1$ (0.1-35 μm)/ $R_2$(0.25/0.45-87.5 μm) Dispersive pressure: 3 bar 10 mm/s | | | Particle volume over particle size VMD (Volume mean diameter in μm) |
|---|---|---|---|---|---|
| | | X10 | X50 | X90 | |
| FII | Raw (pre-milled) | 0.94 | 3.79 | 44.75 | 14.70 |
| | Jet milled | 0.61 ± 0.01 | 1.79 ± 0.03 | 3.95 ± 0.04 | 2.07 |
| FIII | Raw (pre-milled) | 1.03 | 4.33 | 11.46 | 5.52 |
| | Jet milled | 0.63 ± 0.01 | 2.06 ± 0.02 | 4.50 ± 0.12 | 2.38 |

The $X_{90}$ particle size distribution post-milling was similar for both forms of linezolid.

4.2. Suspension of Milled Linezolid Form II and Form III 50 mg of each form was weighed and one mL of poloxamer vehicle was added. The particles were re-suspended by manual shaking for one minute. The Form II air jet milled particles dispersed uniformly. Form III particles formed lumps and were not evenly distributed. This observation indicates that Linezolid Form II was preferred over Form III because of its improved suspension properties.

4.3. Scaled-Up Milling of Linezolid Form II and Particle Size Distributions

Linezolid form II (Symed, India) was air jet milled at 0.5 kg scale to provide micronized linezolid form II for formulation development. Micronisation was achieved using the following method as shown in Table 5.

TABLE 5

Linezolid Form II micronisation

MC Jet Mill 50 (Dec Group)

| Feed rate 25 g/30 seconds | Duration 6.75 mins |
|---|---|
| Venturi pressure 1.6 bar | Mill pressure 1.6 bar |

Drum end d10 = 0.71 um, d50 = 3.11 um, d90 = 8.45 um

Figure 1B:
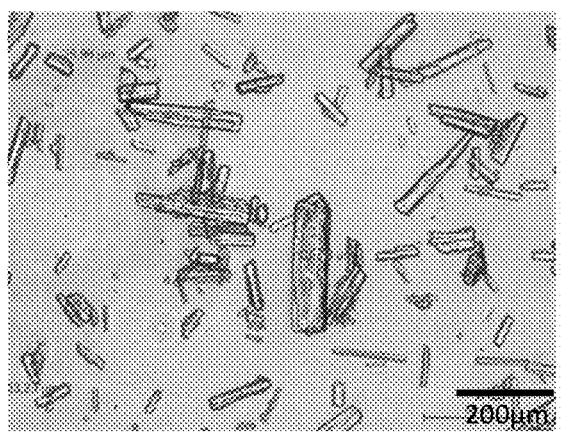
FIG. 1B is representative images of linezolid form II before and after micronisation.
Figure 1B:
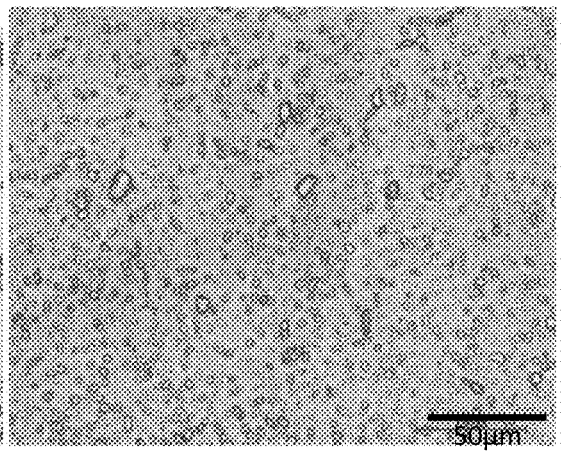

The particle size was analyzed as shown in FIG. 1.

4.4. Sterilization of the API (Active Pharmaceutical Ingredient): Linezolid Form II Sterilization of a milled powder may be achieved by dry heat sterilization or gamma irradiation. Sterilization feasibility studies were performed using glass vials containing 200 mg of milled linezolid Form II.

Dry Heat

Vials containing 200 mg micronized linezolid or spordex discs (AF0558: Steris Life Sciences, UK) were incubated at 120° C. to 160° C. for 2 to 50 hours as indicated in Table 6. The appearance and chemical stability (Method of Example 2) of the linezolid form II powder was assessed at each temperature timepoint. Spore discs were cultured for 7 days at 30-35° C. and growth recorded.

TABLE 6

Sterilization of the API by dry heat

| Temp (° C.) | 120 | 120 | 130 | 130 | 130 | 140 | 140 | 140 | 160 |
|---|---|---|---|---|---|---|---|---|---|
| Time (hr) | 20 | 50 | 8 | 20 | 50 | 4 | 8 | 20 | 2 |
| Appearance | Powder | Powder | Yellow liquid | Yellow liquid | Yellow liquid | Yellow liquid | Powder | Yellow liquid | Yellow liquid |
| Chemical Stability % expected parent (2-8° C. (control) t = 0 | 100 | 99 | 39 | 26 | 19 | 52 | 97 | 17 | 16 |
| Sterility | Sterile | Sterile | Sterile | Sterile | Sterile | Sterile | Sterile | Sterile | Sterile |

Sporedex discs stored at 2-8° C. served as positive controls for bacterial growth which was observed after 1 day of incubation All dry heat conditions tested sterilized the spore discs indicating that >$10^6$ reduction in bioburden was achieved. Except for the 140° C., 8 h treatment, heating linezolid powder above 120° C. caused a physical change from powder to a viscous yellow liquid and a significant reduction in the percentage of linezolid present. The instability in treatments at and above 130° C. suggests that a dry heat sterilization at or around 120° C. may be feasible but technically challenging in a scaled process as minor temperature fluctuation may lead to temperature increase and instability. Sterilization using a relatively low temperature over a prolonged time would require extensive validation and falls outside the standard pharmacopoeia recommendations for dry heat sterilization Gamma Irradiation Vials containing 200 mg micronized linezolid were filled in air or under nitrogen and were subjected to 15 KGy or 25 KGy gamma irradiation at ambient temperature or in the cold by packing with ice. The appearance and chemical stability (Method of Example 2) were assessed at time zero after irradiation and also after 28 days storage at 25° C. or 40° C. to assess longer term stability (Table 7).

Example 5: Optimization of the Delivery Vehicle: Poloxamer Based Gel Vehicle 5.1 Poloxamer Hydrogel Preparation A general procedure is followed to prepare the poloxamer vehicle for linezolid injection. Poloxamer hydrogels are formed using the cold method with modifications of the method described in the art (Schmolka, *Journal of Biomedical Materials Research,* 1972, Vol 6(6): 571-582). The tromethamine pH buffer, the chelator calcium disodium EDTA and the radio-opaque iohexol are first made up in water and then poloxamer 407 is added. The mixture is left in the cold until the poloxamer hydrates to a clear solution. This vehicle for injection is made up on a weight by weight basis. The procedure is iterated to optimize the conditions until a suitable formulation is defined. Target concentrations and ranges for tromethamine, EDTA and iohexol in the final injection linezolid suspension is set using weight and volume.

5.2. Sol-Gel Temperature of Poloxamer Hydrogel with Addition of Iohexol

In one study, three vehicles were prepared starting with different concentrations of iodine provided by iohexol: V150, V170 and V190, and with the same concentrations of tromethamine and $CaNa_2EDTA$. Each vehicle was split into two and Poloxamer 407 was added to at a concentration of

TABLE 7

Sterilization of the API by gamma irradiation

| Under | Air | | | | | | Nitrogen | | | | | |
|---|---|---|---|---|---|---|---|---|---|---|---|---|
| KGy | — | | 15 | | 25 | | — | | 15 | | 25 | |
| Temp | Cold | RT | Cold | RT | Cold | RT | Cold | RT | Cold | RT | Cold | RT |
| Appearance | P | P | P | P | P | P | P | P | P | P | P | P |
| Stability % t = 0 | 100 | 100 | 99 | 99.5 | 100 | 100 | 100 | 99.5 | 100 | 100 | 100 | 100.5 |
| Stability % 25° C. day 28 | 98.1 | 99.5 | 99.4 | 99.4 | 99.6 | 100 | 99.6 | 98.7 | 97.5 | 98.8 | 100 | 99.6 |
| Stability % 40° C. day 28 | 99.6 | 100.1 | 98.0 | 99.1 | 99.7 | 98.9 | 99 | 97.7 | 99.3 | 99.5 | 99.3 | 99.4 |

* Appearance: P = white powder. Stability estimates are the average of duplicates.
T = 0 and after 28 days storage at 25° C. or 40° C.

No gross change in powder physical appearance or color was observed after irradiation in any of the conditions. Chemical stability at 28 days post irradiation was good and within expectations. There was no indication that powder had to be vialed under nitrogen or that samples had to be cooled during irradiation.

Gamma irradiation appeared to offer a robust sterilization method that was within the pharmacopoeia guidelines. The data also suggest that the gamma irradiation does not affect the stability of linezolid. Gamma irradiation is the preferred method for sterilization of vialed milled linezolid form II powder.

12% w/w or 12.5% w/w, respectively. The volumes of the 12% and 12.5% w/w poloxamer vehicles and therefore their densities were slightly different. The sol gel of the 6 formulations assessing the effect of iodine (iohexol) and poloxamer concentrations was assessed. Samples were classified accordingly to their rheological properties as assessed by warming the samples from room temperature to 40° C. in 2° C. intervals and inverting the vial: liquid (L)—when moving rapidly in the direction of gravity, viscous liquid (VL) and VVL—when moving slowly down in the direction of gravity and as a gel (G)—when remaining on the bottom of the vial. The latter was classified as the sol-gel transition temperature (Table 8).

TABLE 8

Poloxamer and iohexol performance in the sol-gel formulations

| | Vehicles | | | | | |
|---|---|---|---|---|---|---|
| | Iohexol (V 150 mg I/mL) | | Iohexol (V 170 mg I/mL) | | Iohexol (V 190 mg I/mL) | |
| Tests | 12% w/w | 12.5% w/w | 12% w/w | 12.5% w/w | 12% w/w | 12.5% w/w |
| Density of Vehicle (g/mL) | 1.1415 | | 1.1706 | | 1.2010 | |
| Density (g/mL) | 1.1682 | 1.1678 | 1.1881 | 1.1872 | 1.2084 | 1.2078 |
| Density Temp (° C.) | 11 | 7 | 8 | 7 | 8 | 8 |
| Osmolality Mosmol/L | 500 ± 14.1 | 492 ± 5.7 | 575 ± 23.3 | 589 ± 13.43 | 673 ± 7.5 | 687 ± 3.5 |
| Iohexol % w/w | | 24.0 | | 27.0 | | 30.0 |
| Iohexol mg/ml | | 274.08 | | 316.17 | | 360.30 |
| pH of vehicle | 8.05 | | 8.05 | | 8.06 | |
| pH Temp (° C.) | 17.9 | | 18 | | 20.6 | |
| pH | 7.91 | 7.89 | 7.92 | 7.90 | 8.07 | 8.08 |
| pH Temp (° C.) | 20.2 | 20.4 | 20.6 | 21.3 | 21.1 | 20.5 |
| Sol gel | | | | | | |
| 28° C. | L | L | L | L | L | G |
| 30° C. | L | L | L | L | VL | |
| 32° C. | L | VL | VL | G | VL | |
| 34° C. | L | G | VL | | VL | |
| 36° C. | L | | VL | | G | |
| 38° C. | L | | VVL | | | |
| 40° C. | L* | | VVL* | | | |

*Samples do not gel
L = liquid; G = gel; VL = viscous liquid and VVL = very viscous liquid Osmolarity increases with an increase in iohexol and poloxamer content. The density had also increased with an increase in iohexol concentration. However, the densities of 12% w/w and 12.5% w/w poloxamer for the same vehicle are similar (Table 8).

With a starting concentration of 150 mg I/ml or 170 mg I/ml and 12.5% w/w poloxamer 407, the target solution gelling temperature at 32-34° C. for the vehicle was achieved. However, with 190 mg I/ml, the vehicle gels at 36° C. with 12.0% w/w poloxamer 407 and gels at 28° C. with 12.5% w/w poloxamer 407, suggesting that an optimal poloxamer 407 concentration would be between 12.0% and 12.5% w/w in the vehicle having 190 mg I/ml.

5.3 Linezolid Poloxamer Formulation Development

Linezolid micronized powder prepared as described in Example 4 is mixed with poloxamer solution just prior to administration. The target final concentration of linezolid at injection is set at 50 mg/ml. The 50 mg/ml linezolid concentration can be achieved by resuspending ~200 mg of linezolid powder in approximately 3.8 ml of poloxamer vehicle to give a final volume of approximately 4.0 ml. Other quantities of linezolid and poloxamer vehicle could achieve the same concentration e.g. 100 mg linezolid with 1.9 ml of poloxamer vehicle.

5.4 Procedures for Formulation Preparation

Another study was performed to test addition of the API (linezolid) to the poloxamer vehicle. A 300 g poloxamer vehicle (Table 9) was prepared following the method of manufacture set forth below.

TABLE 9

Preparation of Iohexol containing solution

| | Vehicle | |
|---|---|---|
| Material | % w/w | Mass (g) required for the 300 g vehicle |
| Iohexol | 32.743 | 98.229 |
| Tromethamine | 0.122 | 0.366 |
| Calcium disodium EDTA | 0.011 | 0.033 |
| Deionized Water & pH adjustment to pH 8.0 | 67.124 | 201.372 |
| Total | 100% | 300 g |

Step A: Method of manufacturing 300 g iohexol-containing solution:
1. Recording the tare weight of a 500 mL beaker and adding 150 g of water to the beaker;
2. Dispensing the required mass of tromethamine, calcium disodium EDTA, and iohexol (Table 9) into the beaker, and recording the mass of each component added;
3. Mixing the mixture until all the solids are completely dissolved, and optionally adding a further water to aid dissolution If there is not enough water to dissolve the solids;
4. Weighing the beaker and then adjusting the pH to 8.0 using 5M HCl. If the pH is already close to pH8.0 then it may be necessary to prepare a less concentrated HCl solution.
5. Recording the amount of acid used to adjust the pH by recording the weight of the beaker;
6. Add the remaining water so that the total product weight is 300 g;
7. Recording the appearance and measure the density in duplicate; and
8. Calculating the % w/v Gel formulation by multiplying the actual values for the % w/w of the excipients by the density value in g/mL;

The 300 g vehicle was split to three parts and poloxamer 407 was added as indicated in Table 10, following the method for manufacturing poloxamer gel.

TABLE 10

Poloxamer solution preparation

|  | Gel 1 | | Gel 2 | | Gel 3 | |
| --- | --- | --- | --- | --- | --- | --- |
| Material | % w/w | Mass (g) required for 100 g preparation | % w/w | Mass (g) required for 100 g preparation | % w/w | Mass (g) required for 100 g preparation |
| Poloxamer | 12.00 | 12.00 | 12.25 | 12.25 | 12.50 | 12.50 |
| Vehicle (Step A) | 88.00 | 88.00 | 87.75 | 87.75 | 87.50 | 87.50 |
| Total | 100.00% | 100.00 g | 100.00% | 100.00 g | 100.00% | 100.00 g |

Step B: Method of manufacturing poloxamer-iohexol solution:
1. Weighting the required mass of vehicle (from step A) for each gel into a 150 ml beaker (Table 10) and placing the three beakers in the fridge for at least 1 hour to cool;
2. Adding slowly the required amount of Poloxamer 407, at ambient temperature, to the cold vehicle using an overhead stirrer until the mixture is homogeneous; and recording the appearance;
3. Placing the beakers in the fridge overnight;
4. Checking on the next day that a clear solution has been formed and mix carefully using a spatula or similar to ensure the solution is homogenous;
5. Measuring the density using an Aluminium pycnometer; and recording the appearance and storing the total sample in the fridge until required for testing; and
6. Calculating the % w/v Gel formulation by multiplying the actual values for the % w/w of the excipients by the density value in g/mL.

At first, a sol-gel transition test was performed using 2×5 ml samples of each Gel 1, Gel 2 and Gel 3. If the sol-gel temperature is between the target temperatures of 30-34° C., airjet milled GMP linezolid powder was added to generate a solution containing 50 mg/ml linezolid and tested the sol-gel temperature again as follows.
1. Dispensing 200 mg of milled linezolid into two tared clear 8 mL vials;
2. Adding 3.8 mL of the Gel 1, Gel 2 or Gel 3 prepared above, into each vial; and
3. Shaking the vials vigorously to suspend the API (linezolid) and record the appearance.

TABLE 11

Linezolid poloxamer formulations

|  | Linezolid suspension with Gel 1 | Linezolid suspension with Gel 2 | Linezolid suspension with Gel 3 |
| --- | --- | --- | --- |
| Poloxamer % (w/w) | 12.0 | 12.25 | 12.5 |
| Sol gel ° C. | 38 | 36 | 34 |

The 12.5% w/w poloxamer gel made with a solution containing 32.743% (w/w) Iohexol provided the target sol-gel temperature (34° C.) for the 50 mg/ml linezolid suspension.

Example 6: Preparations of Poloxamer Delivery Vehicles

The delivery vehicle comprising 12.5% w/w poloxamer 407 and 32.7% w/w iohexol (as tested in Example 5) was prepared at an intermediate scale and then at a larger scale to test the tolerance and long term stability of the formulation. These additional batches provide evidence of reproducibility.

TABLE 12

Materials

| Material | % w/w | Mass (g) required for 400 g preparation |
| --- | --- | --- |
| Iohexol | 32.743 | 130.972 |
| Tromethamine | 0.122 | 0.488 |
| Calcium disodium EDTA | 0.011 | 0.044 |
| Deionized Water & pH adjustment to pH 8.0 | 67.124 | 268.496 |
| Total | 100% | 400 g |

Method for the manufacture of a 400 g poloxamer vehicle for injection includes the steps of:
1. Recording the tare weight of a 600 mL beaker; and adding 200 g of water to the beaker;
2. Dispensing the required mass of tromethamine, calcium disodium EDTA, and iohexol (Table 12) into the beaker; and recording the mass of each component added;
3. Mixing the mixture until all the solids are completely dissolved and adding a further water to aid dissolution if necessary;
4. Weighing the beaker and then adjusting the pH to 8.0 using 5M HCl;
5. Adding the remaining water so that the total product weight is 400 g;
6. Recording the appearance and measuring the density in duplicate;
7. Calculating the % w/v Gel formulation by multiplying the actual values for the % w/w of the excipients;
8. Weighing 175 g of Iohexol solution (step 6 above) into a 250 mL beaker and placing the beaker in the fridge for at least 1 hour to cool;

9. Adding slowly 25 g of Poloxamer 407 (BASF Kolliphor 407: Batch no: WPNK538B (R/003191)), at ambient temperature, to the cold iohexol solution using an overhead stirrer until the mixture is homogeneous;
10. Placing the beaker in the fridge overnight; and checking next day that a clear solution has been formed and mix carefully using a spatula or similar to ensure the solution is homogenous;
11. Measuring the density using an Aluminium pycnometer on a 30 mL sample; and recording the appearance and storing the total sample in the fridge until required for testing; and
12. Calculating the % w/v Gel formulation by multiplying the actual values for the % w/w of the excipients by the density value in g/mL.

The poloxamer solution was sterilized by filtration using a Watson-Marlow peristaltic pump. The poloxamer solution was filtered through a Sartopore 2, 0.4 µm filter (Part No. 5441307H4 G). The quantities of poloxamer and iohexol and the sol-gel temperature of the gel were assessed pre and post filtration to establish whether iohexol was retained by the filter or if performance of the gel was altered by filtration (Table 13).

TABLE 13

Assay results for the gel pre and post filtration

| Sample | Test | Timepoint | Result |
| --- | --- | --- | --- |
| Poloxamer vehicle | Density (pre filtration) | Day 1 | 1.97 g/cm$^3$ |
| | Density (post filtration) | Day 1 | 1.207 g/cm$^3$ |
| | Iohexol assay (pre filtration) | Day 1 | 27.1% w/w |
| | Iohexol (post filtration) | Day 1 | 27.5% w/w |
| | Sol gel | Day 1 | 34° C. |
| | | Day 3 | 34° C. |
| | | Day 7 | 34° C. |
| | | Day 14 | 34° C. |

The pre and post filtration results indicated that the gel could be filtered using a peristaltic pump and that the composition of the gel and its performance was not altered by filtration. The differences in assay results pre and post filtration are within the assay tolerances and specifications. Filtration is the preferred method for gel sterilization.

Linezolid was then loaded into the gel and tested for sol-gel temperature. The results were shown in Table 14, indicating that the suspension prepared at an intermediate scale retains the required sol-gel temperature.

TABLE 14

Sol-gel temperature of linezolid suspension

| Sample | Test | Timepoint | Result |
| --- | --- | --- | --- |
| Linezolid Suspension in Poloxamer vehicle 3.8 ml poloxamer vehicle plus 200 mg linezolid | Linezolid assay | Day 1 | 47.7 mg/ml |
| | Sol gel | Day 1 | 34° C. |
| | | Day 3 | 34° C. |
| | | Day 7 | 34° C. |
| | | Day 14 | 34° C. |

Example 7: In Vivo Pharmacokinetics and Efficacy of Linezolid Formulations

A pilot study was performed to test the in vivo pharmacokinetics and efficacy of linezolid suspensions prepared following the manufacture methods descried herein.

Figure 3:
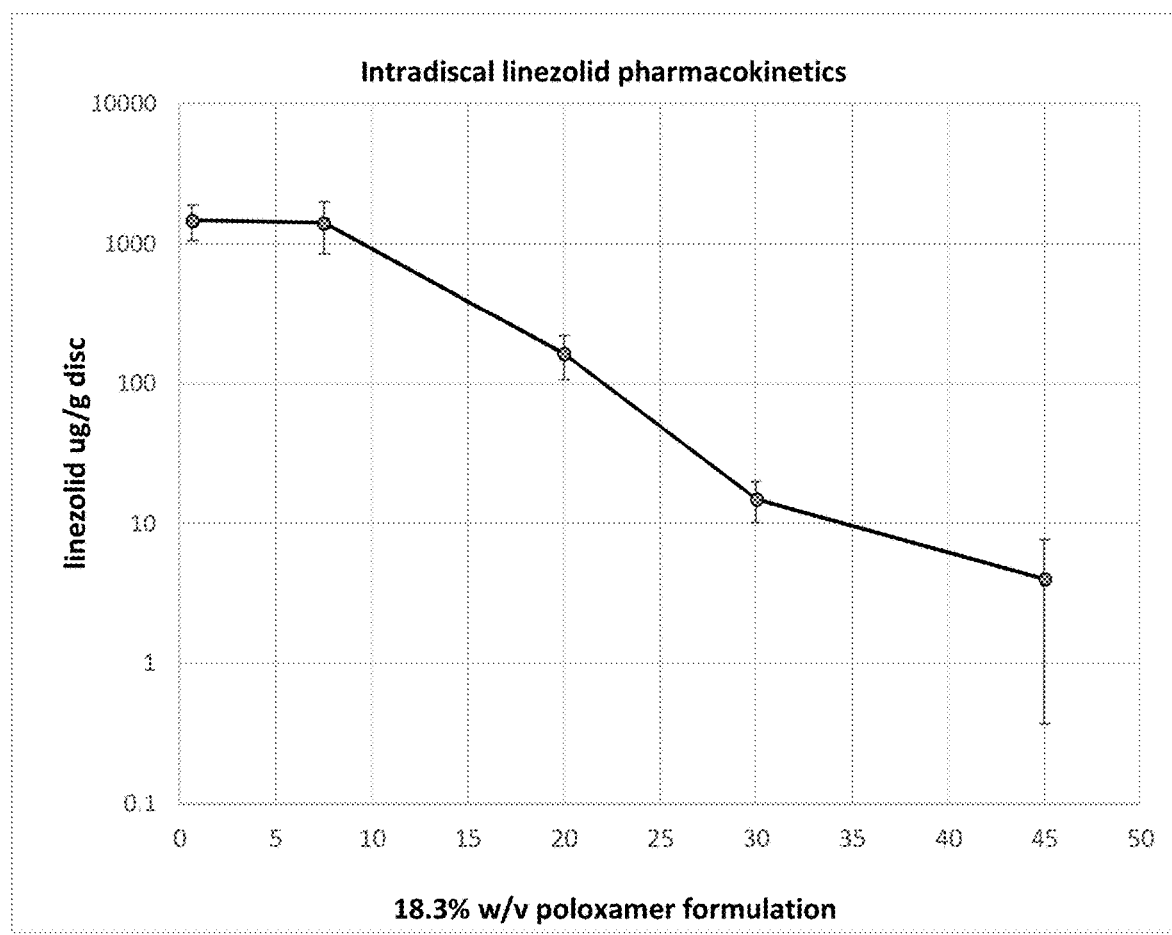
FIG. 3 demonstrates the amount of linezolid recovered from sheep disc after intradiscal administration. Each point shows mean and standard error of the mean based on 3-4 discs.

A delivery vehicle containing 16.6% (w/w) poloxamer containing a 50 mg/ml linezolid suspension was prepared following the manufacture methods described in Examples 2-5. 0.1 ml of this linezolid suspension was injected into sheep disc as described in Example 1. As shown in FIG. 2, using iohexol in the formulation can allow visualization of the formulation being injected. The linezolid pharmacokinetics after intradiscal administration were measured. FIG. 3 shows the amount of linezolid recovered from sheep discs after injection at a dose of 5 mg linezolid per disc.

Figure 4:
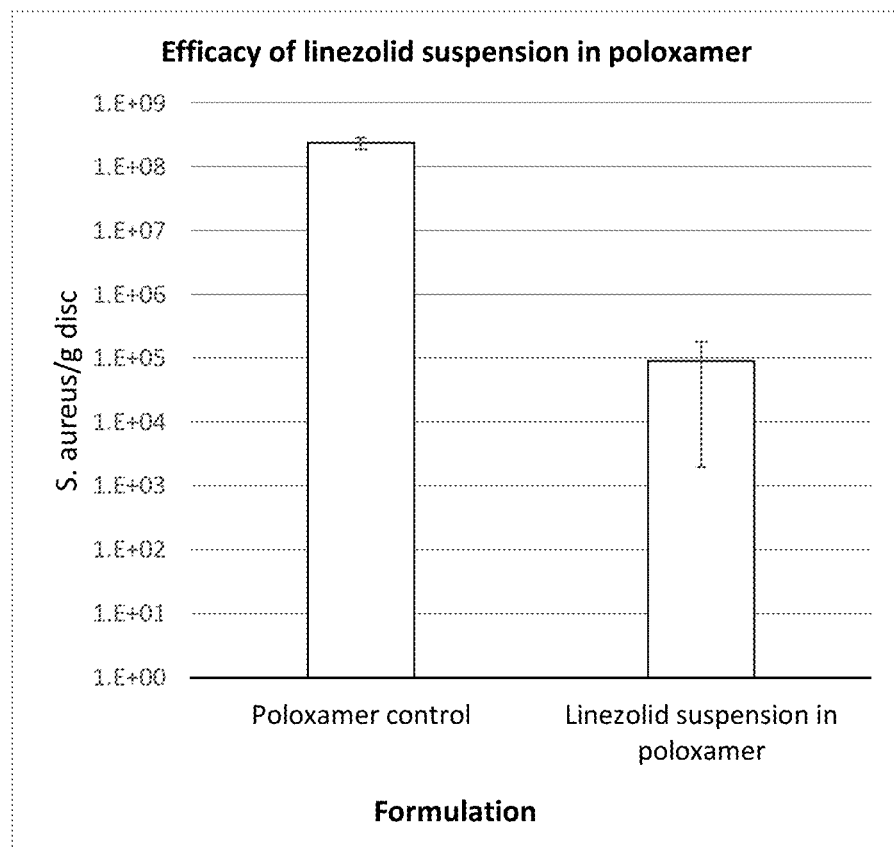
FIG. 4 shows the bacteria isolated from linezolid treated discs as compared to untreated discs.

The efficacy of the tested linezolid suspension as shown in FIG. 4 indicates that administration of the linezolid suspension reduced average bacterial burden per disc by >3 logs (P=0.009). More than 60% of discs in the treated group were sterile. Those with bacteria remaining has a significant reduction in burden.

Example 8: Injectability of the Linezolid Formulation

The injectability of the suspension is evaluated using a fine bore 25 gauge needle that is longer than expected to be required for human administration (4.69 inch) in order to ensure that the suspension will not block the needle or be too viscous to pass through the syringe. The hydrogel alone or a linezolid suspension is made up and a 1 ml luer lock syringe is primed with the formulation. The needle is positioned and the gel or suspension is injected out through the needle. The results are recorded as follows: 1=injection not possible; no flow; or 2=injection possible; drop-wise flow; or 3=injection: moderate; continuous flow. Gel and suspensions scoring 2 or 3 are within specification.

Example 9: Scale-Up Preparation of Linezolid Suspension Formulation

Further, the linezolid suspension in poloxamer-iohexol delivery solution that is optimized herein is manufactured in larger scale and under current Good Manufacturing Practice (cGMP) standards. The formulation is sterile and ready for clinical use.

9.1 Micronisation and Vialing of Linezolid Form II (API)

To reduce the size of the linezolid form II to make them form a suspension in the formulation and pass through administration needles, linezolid form II were micronized by airjet milling. Linezolid form II large crystals (about 1-2 kilogram) were micronized under nitrogen using a LaboMill jet miller (F.P.S. Food and Pharma Systems s.r.l, Italy) with a feed rate of 60 g/min to 160 g/min, a mill pressure of 2 to 4 bar, and a venturi pressure of 2 to 4 bar. The particle size distribution of the raw and air-jet milled material was analyzed by laser diffraction (Sympatec GmbH, Helos Disperse). The data on the size distribution for unmilled powder (R1) and milled powder (R4) were collected and analyzed. Air jet milling reduced the particle size from D10 4 to 6 µm (D10, 10% of the mass of the sample is comprised of particles with diameter less than this range) and D90 40 to 50 µm (D90, 90% of the mass of the sample is comprised of particles with is diameter less than this range) particle size distribution to a D10 0.4 to 0.50 µm and D90 4 to 5 µm. Specifications for the micronized Linezolid form II were set at D10 0.2 to 1.0 µm, D90 3 to 10 µm. At 1 kg to 1.5 kg scale, micronisation provided 87% to 89% yield of in specification linezolid form II powder.

The micronized linezolid form II powder was filled into 10 ml Schott Type I tubular clear glass vials at 253 mg±2 mg per vial by hand and closed with West 4023/50 grey bromobutyl elastomeric stoppers which are FluroTec® coated on the product contact surface and capped with aluminum seals. Approximately 608 g of micronized linezolid form II filled approximately 2400 vials (Intermediate drug product: PP353-A).

9.2 Sterilization of Linezolid (FII)

The ~2400 vials were sterilized by gamma irradiation using a Cobalt 60 source at ~23.5±10% kGy at ambient temperature. Irradiated vials of linezolid form II were labelled as PP353-A. The sterility of the irradiated linezolid form II powder was tested according to the pharmaceutical sterility requirements (EP 2.6.1).

The content of 20 vials (20×253 mg linezolid) was dissolved in 2500 ml sterile water by incubating at 35-39° C. while shaking (±200 rpm) until the product was dissolved. 200 ml of linezolid solution was filtered through a Durapore Steritest device pre-wetted with Fluid D (including 1.0 g Peptic digest of animal tissue, 1 ml Polysorbate 80, 1000 ml purified water, pH: 7.1±0.2). Each membrane was washed 5 times with 100 ml Fluid D. One canister was filled with 100 ml TSB+1% Tween+0.07% Lecithine (including 17.0 g pancreatic digest of casein, 3.0 g papaic digest of soya bean, 5.0 g sodium chloride, 2.5 g dipotassium hydrogen phosphate, 2.5 g glucose monohydrate, 10 ml Polysorbate80, 0.7 g Lecithine, 1000 ml purified water, pH7.3±0.2) and incubated at 20-25° C. for 14 days. The other canister was filled with 100 ml FTM (Fluid thioglycollate)+1% Tween+0.07% Lecithine (including 0.5 g 1-cystine, 0.75 g granulated agar, 2.5 g sodium chloride, 5.5 g/5.0 g glucose monohydrate/anhydrous, 5.0 g yeast extract, 15.0 g pancreactic digest of casien, 0.5 g sodium thioglycollate or 0.3 ml thioglycollic acid, 1.0 ml resazurin sodium solution freshly prepared, 10 ml Polysorbate 80, 0.7 g Lecithine, 1000 ml purified water, pH7.1±0.2) and incubated at 30-35° C. for 14 days. All the solutions were sterilized using a validated process. After 14 days incubation there was no growth in the samples indicating that the PP353-A samples were sterile.

9.3 Scale-Up Preparation of the Diluent (Delivery Vehicle)

Formulation of delivery solution (Poloxamer 407-iohexol solution) was performed at 18.4 L (~22 kg) scale, followed by sterilization by aseptic filling into 10 mL Schott Type I clear glass vials at a target fill weight of 8.40 g (equivalent to a 7 mL nominal fill volume). A preparation size of up to 2400 vials was made and referred as intermediate drug product PP353-B.

TABLE 15

Formula for delivery vehicle solution (PP353-B)

| | |
|---|---|
| Poloxamer Kolliphor 407 | 149.50 g |
| Iohexol | 342.65 g |
| Calcium disodium EDTA | 0.100 g |
| Tromethamine | 1.210 g |
| 1M hydrochloric acid solution | As required |
| Water for Injection (WFI) | To 1196.0 g |
| Intermediate formulation pH target (the pH value prior to Poloxamer addition and final formulation to target weight) | pH 8.00 ± 0.20 |

The 22 kg preparation of the delivery solution (PP353-B) was prepared following the steps of:
1. Adding 22.257 g tromethamine to 11,500 g pre-chilled (5° C.) WFI in a 20 L vessel and stirring until tromethamine is dissolved;
2. Adding 1.839 g calcium disodium EDTA and stirring until it is dissolved and subsequently adding 6,303 g iohexol and stirring until dissolved;
3. (optional) Adjusting the pH of the solution to about pH8.0 (acceptable range pH7.80-pH8.20) with 1M hydrochloric acid;
4. Adding additional pre-chilled WFI to a net weight of 18,750 g;
5. Adding 2,750 g Poloxamer 407 slowly, in approximately 100 g portions, with stirring; and allowing any clumped poloxamer to break up and disperse prior to further additions; and
6. Adding additional pre-chilled WFI to a final target weight of 22,000 g equivalent to a nominal 18.4 L and Stir until poloxamer is solubilized.

The formulation was chilled as poloxamer dissolves faster and has lower viscosity at lower temperatures. The final PP353-B poloxamer solution has a density of 1.196 g/mL at 15° C.

The chilled PP353-B product was sterilized by double filtrations. The solution (PP353-B) was flowed using a peristaltic pump first through a Sartopore 2 XLG Midicap filter into an 8-glove, general purpose filling isolator, then through a second in-line Sartopore 2 XLG Midicap filter. The solution was chilled to reduce viscosity through the pump and filters. The sterile PP353-B was held at 15° C. in 10 L vessels within the isolator. This temperature control was set to define the density and gravimetric fill of the vials. The sterile solution was packed into 10 ml Schott Type I tubular clear glass vials at 7.0 mL (8.4 g) of the sterile solution per vial using a Masterflex pump and closed with West 4023/50 grey bromobutyl elastomeric stoppers which are FluroTec® coated on the product contact surface and capped with aluminium seals. The 22 kg solution (PP353-B) filled approximately 2400 vials.

The sterility of PP353-B was tested according to the requirements stated in the EP 2.6.1. Twenty vials of PP353-B were apportioned between two Steritest canisters and filtered. Each canister was washed with approximately 300 ml of Fluid A (0.1% peptone water). The Steritest canisters were filled with 100 ml of TSB or FTM medium and incubated for 14 days. Absence of growth in the cultures indicates sterility of PP353-B.

9.4 Rheological Properties of the Diluent

The transition temperature of the PP353-B solution was assessed in triplicate according to the sol-gel method described below:
1. Preparing a jacketed vessel containing deionised water and connect the vessel to a re-circulating water bath;
2. Setting the temperature of the water bath to 22° C., and measuring the temperature in the jacketed vessel using a calibrated thermometer or thermoprobe;
3. Placing the samples into the jacketed vessel when the water in the jacketed vessel is at 22° C. and stable (±0.5° C. for at least 5 minutes);
4. Allowing the samples 15 to 20 minutes to equilibrate to 22° C.;
5. Removing the vials from the jacketed vessel and immediately inverting to assess the liquid-gel behavior; and Immediately classifying the samples according to their visual rheological properties: 1). liquid when moving rapidly in the direction of gravity; 2). viscous Liquid when moving slowly down in the direction of gravity and 3). gel when remaining on the bottom of the vial;
6. (optional) Resuspending the samples and transferring back into the jacketed vessel as soon as possible ff the samples haven't gelled; and increasing the temperature of the water bath by 2° C.;
7. Recording the liquid-gel behavior;

8. Allowing the samples an additional 15 minutes to equilibrate to the same temperature, once the temperature of the water in the jacketed vessel is stable (±0.5° C.) for 5 minutes; and
9. Repeating steps (5), (6), (7) & (8) above until the temperature reaches 40° C.

The sol-gel transition temperature of all three tested vials of the PP353-B solution was 28° C.

9.5 Preparation of Linezolid Form II Suspension Formulation

Vials containing micronized and sterile linezolid powder (API) that were prepared according to the steps described above (9.1 and 9.2) (i.e. PP353-A) were used to prepare linezolid suspensions. Each vial contains 253 mg API. Vials containing the sterile solution prepared according to the method described above (9.3 and 9.4) (i.e. PP353-B) were used as the diluent. Each vial contains 7 mL of PP353-B diluent.

To make the linezolid suspension, an approximately 4.8 mL of PP353-B solution was transferred into a vial of PP353-A. The vial was mixed by shaking until there is no solid powder observed (about 1-1.5 minutes). The process was carefully carried to avoid increasing the vial temperature. The final volume of one reconstituted vial is approximately 5 mL. The final linezolid suspension in the diluent is labelled as drug product PP353.

The sol-gel transition temperature of the PP353 suspension was assessed in triplicate according to the sol-gel method described in Section 9.4.

The sol-gel transition of all three tested vials (PP353) was 28° C. It was noted that smaller scale non-GMP products of the poloxamer hydrogel and linezolid suspension formulations have higher sol-gel transition temperatures at 32° C. to 36° C. (Examples 5 and 6), while the gel and linezolid suspensions prepared in large scale GMP products have a lower sol gel transition temperature at 28° C. The results indicate that poloxamer based hydrogel solutions and linezolid suspensions have a wide range of sol-gel transition temperatures, at least from about 28° C. to about 36° C.

Example 10. Injectability of the Linezolid Formulation Suspension (PP353)

The linezolid suspensions made from this GMP scale preparation (PP353) were further tested the injectability to access the formulation to pass through an injection needle to enable administration. In this study, the injectability of the suspension (PP353) was tested using a double needle technique and a warmed sweet potato as a surrogate for patient's flesh.

Figure 5:
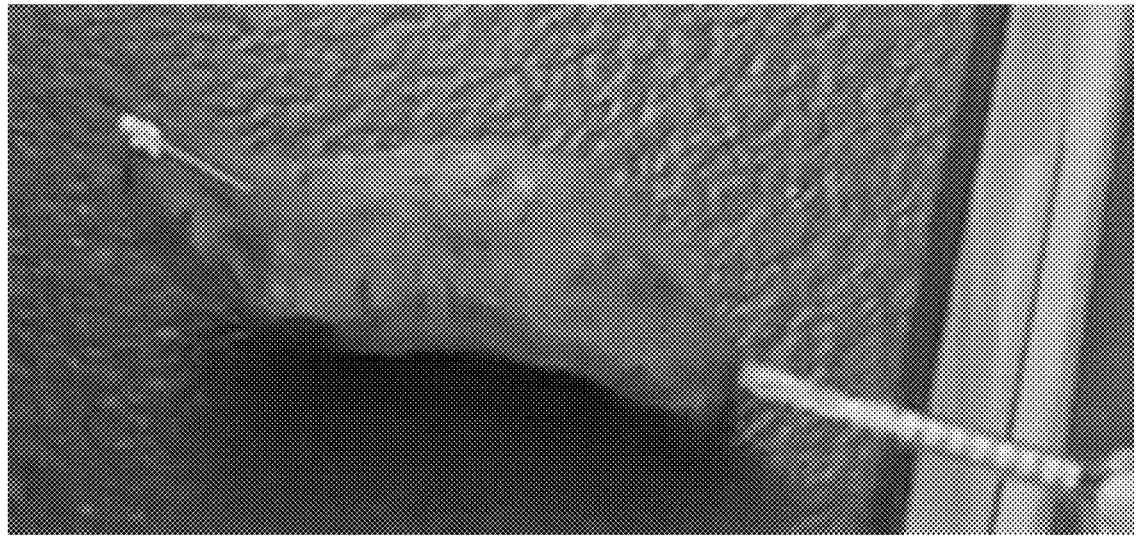
FIG. 5 demonstrates the injectability of the linezolid suspension (PP353) through a pre-warmed sweet potato.

A sweet potato was warmed 37° C. in a water bath. A 5 inch (127 mm) 18 French gauge needle was placed through the sweet potato. This needle represents a guide needle that would be positioned in a patient under image guidance using fluoroscopy such that the needle point is adjacent to the disc to be injected. Another 7 inch (178 mm) 22 French gauge needle was then inserted through the guide needle until the end protrudes from the 5 inch guide needle. This needle represents the administration needle that would be inserted into the disc to be injected. The two needles were allowed to warm to 37° C. in the sweet potato. A 1 mL syringe filled with the linezolid suspension (from PP353) which was at room temperature, was attached to the administration needle. The suspension was then injected through the warm needle and It was observed that the suspension extruded from the needle as a gel, rather than a dropwise liquid (FIG. 5). This experiment demonstrated that the linezolid suspension with a lower sol-gel transition temperature (i.e., PP353 at 28° C.) can be injected through a warm administration needle and during the process, it is transforming from liquid to gel inside the needle.

This observation indicates that clinically, the injection of a preformed hydrogel is likely to localize administration to the site of administration and minimize any extravasation from the injection site, e.g., the spinal disc of a patient.

Example 11. The Systemic Pharmacological Profile of PP353 Linezolid Suspension

To measure the systemic pharmacologic profile of the PP353 product, sheep (n=27, 3 for each experimental group) were dosed with the linezolid suspension (PP353) by intradiscal disc injection following the injection procedure described in the section 1.3 of Example 1. X-ray images were taken throughout the injection procedure to identify target vertebral discs to aid the injection procedure and as a gauge of successful dosing. The PP353 linezolid formulation (0.1 ml suspension containing 5 mg linezolid) was injected into two discs in a sheep. The same volume of the poloxamer-iohexol delivery vehicle (i.e. PP353-B) (0.1 ml) was dosed to sheep in the control groups. Blood samples were taken at 0 mins (prior to administration of the test material) and 15 mins, 30 mins, 1 hour, 2 hours, 4 hours, 8 hours, 16 hours, 30 hours and 48 hours post dosing.

Figure 6:
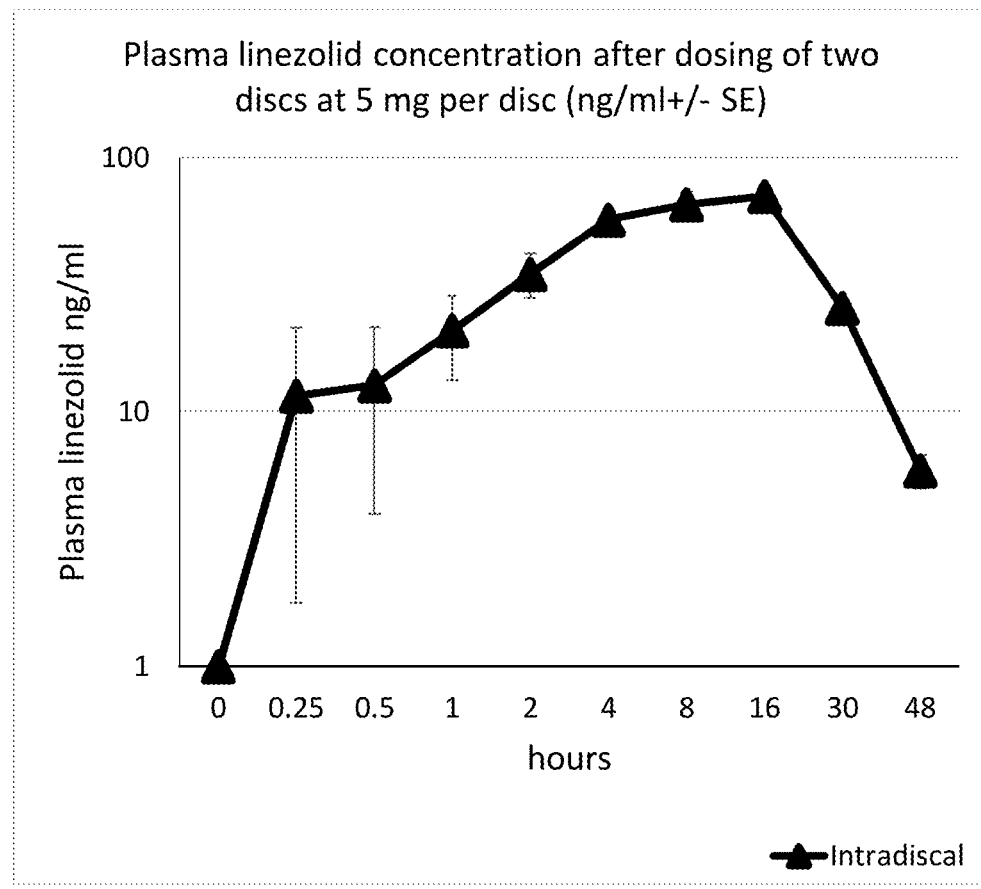
FIG. 6 depicts the pharmacokinetics of linezolid in sheep administrated with PP353 linezolid suspensions. The Y-axis represents the concentration of plasma linezolid in ng/ml. The X-axis represents time in hours.

All the blood samples were processed and the concentration of linezolid in the plasma extracts was measured and determined using LC-MS/MS following the GLP (Good Laboratory Practice for nonclinical laboratory studies) regulations. As shown in FIG. 6, the concentration of linezolid in plasma depicts a similar pattern as observed previously with the experimental formulation products (e.g., Examples 4-7). The small injection volume (e.g., 0.1 ml) of the suspension to sheep discs may minimize a potential depot effect.

In summary, these observations provide evidence for the in vivo injectability of the formulation with a relatively lower gelling temperature (e.g., 28° C.) and the release of linezolid from the formulation into surrounding tissues and blood.

The invention claimed is:

1. An injectable pharmaceutical formulation comprising:
   (a) 2.5% to 20% of linezolid Form II by weight of the formulation,
   (b) a thermosensitive hydrogel comprising 9.5% to 17% poloxamer 407 by weight of the formulation and 14% to 59% iohexol by weight of the formulation, and optionally
   (c) at least one pharmaceutically acceptable excipient, wherein linezolid Form II forms a suspension in the thermosensitive hydrogel and has particle size distribution of D90≤10 μm.

2. The injectable pharmaceutical formulation of claim 1, wherein said poloxamer 407 is present from 10.8% to 12.8% by weight of the formulation.

3. The injectable pharmaceutical formulation of claim 2, wherein iohexol is present from 17% to 30% by weight of the formulation.

4. The injectable pharmaceutical formulation of claim 3, wherein the suspension gels at a temperature from about 26° C. to about 38° C.

5. The injectable pharmaceutical formulation of claim 4, wherein the suspension gels at a temperature from about 32° C. to about 36° C.

6. The injectable pharmaceutical formulation of claim 4, wherein the suspension gels at a temperature from about 26° C. to about 32° C.

7. An injectable pharmaceutical formulation comprising 2.5% to 20% linezolid Form II by weight, 17% to 30% iohexol by weight, and 10.8% to 12.8% poloxamer 407 by weight of the formulation, wherein linezolid Form II forms a suspension.

8. The injectable pharmaceutical formulation of claim 7, wherein the injectable pharmaceutical formulation is prepared for administering to an intervertebral disc, an intervertebral space, an intra-articular space, a site adjacent to bone edema, a ligament, bone, joint, or tendon associated with the spine, or a tendon and bone junction.

9. The injectable pharmaceutical composition of claim 8, wherein the bone, joint, ligament, or tendon associated with the spine is associated with a cervical, thoracic, lumbar or sacral vertebra.

10. An injectable linezolid formulation comprising:
    (a) a linezolid Form II powder,
    (b) a thermosensitive hydrogel comprising 9.5% to 17% poloxamer 407 by weight of the formulation and 14% to 59% iohexol by weight of the formulation, and optionally
    (c) at least one excipient,
    wherein said linezolid formulation is prepared through the method comprising:
    (i) milling linezolid Form II to a defined powder with particle size distribution of D90≤10 μm,
    (ii) preparing a unit of linezolid powder from step (i) and sterilizing the preparation,
    (iii) preparing and sterilizing the thermosensitive hydrogel comprising poloxamer 407 and iohexol, and
    (iv) suspending said linezolid Form II powder from step (ii) in the thermosensitive hydrogel from step (iii).

11. The injectable linezolid formulation of claim 10, wherein the linezolid powder is sterilized by gamma irradiation.

12. The injectable linezolid formulation of claim 11, wherein the steps (iii) and (iv) are performed at a lower temperature than the steps (i) and (ii).

13. A kit comprising:
    (a) a linezolid Form II powder with particle size distribution of D90≤10 μm, and
    (b) a thermosensitive hydrogel comprising 9.5% to 17% poloxamer 407 by weight and 14% to 59% iohexol by weight,
    wherein the linezolid Form II powder is at an amount to give a concentration of 2.5% to 20% of linezolid by weight.

14. The kit of claim 13 further comprising a syringe and a needle for injection.

* * * * *